US006660229B2

(12) United States Patent
Cantor et al.

(10) Patent No.: US 6,660,229 B2
(45) Date of Patent: Dec. 9, 2003

(54) USE OF NUCLEOTIDE ANALOGS IN THE ANALYSIS OF OLIGONUCLEOTIDE MIXTURES AND IN HIGHLY MULTIPLEXED NUCLEIC ACID SEQUENCING

(75) Inventors: Charles R. Cantor, Del Mar, CA (US); Fouad A. Siddiqi, Boston, MA (US)

(73) Assignee: The Trustees of Boston University, Boston, MA (US)

( * ) Notice: Subject to any disclaimer, the term of this patent is extended or adjusted under 35 U.S.C. 154(b) by 0 days.

(21) Appl. No.: 09/880,988

(22) Filed: Jun. 13, 2001

(65) Prior Publication Data

US 2002/0045178 A1 Apr. 18, 2002

Related U.S. Application Data

(60) Provisional application No. 60/211,356, filed on Jun. 13, 2000.

(51) Int. Cl.[7] .................. B32B 27/04; B32B 27/12; G05B 17/00; G01N 23/00; G01N 21/72
(52) U.S. Cl. ................. 422/71; 422/70; 422/78; 422/68.1; 422/80; 422/116; 436/59; 436/155; 436/161
(58) Field of Search .................. 422/71, 78, 68.1, 422/80, 116, 70; 436/59, 155, 161

(56) References Cited

U.S. PATENT DOCUMENTS

| | | | | |
|---|---|---|---|---|
| ,005,478 | A | 1/1848 | Hillenkamp | 250/288 |
| 3,553,452 | A | 1/1971 | Tiernan et al. | 250/41.9 |
| 3,776,700 | A | 12/1973 | Gallant | 422/65 |
| 3,807,235 | A | 4/1974 | Lefkovitz | 73/863.32 |
| 3,931,516 | A | 1/1976 | Fletcher et al. | 250/281 |
| 4,047,030 | A | 9/1977 | Lobach | 250/281 |
| 4,076,982 | A | 2/1978 | Ritter et al. | 250/288 |
| 4,139,346 | A | 2/1979 | Rabbani | 422/56 |
| 4,214,159 | A | 7/1980 | Hillenkamp et al. | 250/288 |
| 4,461,328 | A | 7/1984 | Kenney | 422/100 |
| 4,515,781 | A | 5/1985 | Torrence et al. | 514/46 |
| 4,554,839 | A | 11/1985 | Hewett et al. | 73/864.16 |
| 4,582,789 | A | 4/1986 | Sheldon, III et al. | 435/6 |
| 4,604,363 | A | 8/1986 | Newhouse et al. | 436/177 |
| 4,625,112 | A | 11/1986 | Yoshida | 250/287 |
| 4,663,944 | A | 5/1987 | Bernius et al. | 62/51.1 |
| 4,711,955 | A | 12/1987 | Ward et al. | 536/25.32 |
| 4,733,073 | A | 3/1988 | Becker et al. | 250/288 |
| 4,740,692 | A | 4/1988 | Yamamoto et al. | 250/288 |
| 4,779,467 | A | 10/1988 | Rainin et al. | 73/863.32 |
| 4,806,546 | A | 2/1989 | Carrico et al. | 536/27 |
| 4,826,360 | A | 5/1989 | Iwasawa et al. | 406/51 |
| 4,851,018 | A | 7/1989 | Lazzari et al. | 55/356 |
| 4,877,745 | A | 10/1989 | Hayes et al. | 436/166 |
| 4,882,127 | A | 11/1989 | Rosenthal et al. | 422/50 |
| 4,920,264 | A | 4/1990 | Becker | 250/289 |
| 4,925,629 | A | 5/1990 | Schramm | 422/82.05 |
| 4,952,518 | A | 8/1990 | Johnson et al. | 436/518 |
| 4,988,617 | A | 1/1991 | Landegren et al. | 435/6 |
| 5,000,921 | A | 3/1991 | Hanaway et al. | 422/100 |
| 5,003,059 | A | 3/1991 | Brennan | 536/27 |
| 5,059,654 | A | 10/1991 | Hou et al. | 525/54.1 |
| 5,064,754 | A | 11/1991 | Mills | 436/6 |
| 5,108,703 | A | 4/1992 | Pfost et al. | 422/65 |
| 5,118,605 | A | 6/1992 | Urdea et al. | 436/6 |
| 5,118,937 | A | 6/1992 | Hillenkamp et al. | 250/282 |
| 5,122,342 | A | 6/1992 | McCulloch et al. | 422/65 |
| 5,135,870 | A | 8/1992 | Williams et al. | 436/173 |
| 5,143,451 | A | 9/1992 | Millgard | 374/25 |
| 5,143,854 | A | 9/1992 | Pirrung et al. | 436/518 |
| 5,149,625 | A | 9/1992 | Church et al. | 435/6 |
| 5,164,594 | A | 11/1992 | Thompson et al. | 250/288 |
| 5,174,962 | A | * 12/1992 | Brennan | |
| 5,175,209 | A | 12/1992 | Beattie et al. | 525/54.11 |
| 5,175,430 | A | 12/1992 | Enke et al. | 250/282 |
| 5,198,540 | A | 3/1993 | Koster | 536/25.3 |
| 5,202,231 | A | 4/1993 | Drmanac et al. | 435/6 |
| 5,210,412 | A | 5/1993 | Levis et al. | 648/282 |
| 5,221,518 | A | 6/1993 | Mills | 422/62 |
| 5,237,016 | A | 8/1993 | Ghosh et al. | 525/329.4 |
| 5,242,974 | A | 9/1993 | Holmes | 525/54.11 |
| 5,247,175 | A | 9/1993 | Schoen et al. | 250/281 |
| 5,262,128 | A | 11/1993 | Leighton et al. | 422/100 |
| 5,273,718 | A | 12/1993 | Skold et al. | 422/101 |
| 5,288,644 | A | 2/1994 | Beavis et al. | 436/94 |
| 5,300,774 | A | 4/1994 | Buttrill | 250/287 |
| 5,306,619 | A | 4/1994 | Edwards et al. | 435/6 |
| 5,325,021 | A | 6/1994 | Duckworth et al. | 315/111.51 |
| 5,338,688 | A | 8/1994 | Deeg et al. | 436/180 |
| 5,350,676 | A | 9/1994 | Oberhardt et al. | 435/13 |
| 5,363,883 | A | 11/1994 | Weidmann | 139/450 |
| 5,364,760 | A | 11/1994 | Chu et al. | 435/6 |
| 5,365,063 | A | 11/1994 | Kaesdorf et al. | 250/288 |
| 5,381,008 | A | 1/1995 | Tanner et al. | 250/288 |
| 5,382,793 | A | 1/1995 | Weinberger et al. | 250/288 |
| 5,403,711 | A | 4/1995 | Walder et al. | 435/6 |
| 5,427,929 | A | 6/1995 | Richards et al. | 435/91.2 |
| 5,436,143 | A | 7/1995 | Hyman | 435/91.2 |
| 5,439,649 | A | 8/1995 | Tseung et al. | 422/99 |

(List continued on next page.)

FOREIGN PATENT DOCUMENTS

| | | |
|---|---|---|
| DE | 3221681 | 12/1983 |
| DE | 4431174 | 3/1996 |
| DE | 19617011 | 4/1996 |

(List continued on next page.)

OTHER PUBLICATIONS

US 6,124,129, 9/2000, Szafranski et al. (withdrawn)
Fitzgerald et al., "Basic Matrices for the Matrix–Assisted Laser Desorption/Ionization Mass Spectrometry of Proteins and Oligonucleotides," *Analytical Chemistry* 65; 3204–3211 (1993).

(List continued on next page.)

*Primary Examiner*—Gary Benzion
*Assistant Examiner*—Arun K. Chakrabarti
(74) *Attorney, Agent, or Firm*—Stephanie L. Seidman; Heller Ehrman White & McAuliffe, LLP

(57) ABSTRACT

Methods and kits that use nucleotide analogs to confer increased accuracy and improved resolution in the analysis and sequencing of oligonucleotide mixtures are provided.

40 Claims, 8 Drawing Sheets

U.S. PATENT DOCUMENTS

| | | | |
|---|---|---|---|
| 5,440,119 A | 8/1995 | Labowsky | 250/282 |
| 5,453,613 A | 9/1995 | Gray et al. | 250/281 |
| 5,459,039 A | 10/1995 | Modrich et al. | 435/6 |
| 5,498,545 A | 3/1996 | Vestal | 436/47 |
| 5,503,980 A | 4/1996 | Cantor | 435/6 |
| 5,508,169 A | 4/1996 | Deugau et al. | 435/6 |
| 5,510,270 A | 4/1996 | Fodor et al. | 436/518 |
| 5,512,295 A | 4/1996 | Kornberg et al. | 424/450 |
| 5,512,439 A | 4/1996 | Hornes et al. | 435/6 |
| 5,514,548 A | 5/1996 | Krebber et al. | 435/6 |
| 5,525,464 A | 6/1996 | Drmanac et al. | 435/6 |
| 5,532,227 A | 7/1996 | Golub et al. | 514/152 |
| 5,538,897 A | 7/1996 | Yates et al. | 436/89 |
| 5,547,835 A | 8/1996 | Köster | 435/6 |
| 5,563,410 A | 10/1996 | Mullock | 250/288 |
| 5,578,444 A | 11/1996 | Edwards et al. | 435/6 |
| 5,580,434 A | 12/1996 | Robotti et al. | 204/451 |
| 5,580,733 A | 12/1996 | Levis et al. | 435/6 |
| 5,589,136 A | 12/1996 | Northrup et al. | 422/102 |
| 5,599,500 A | 2/1997 | Jones | 422/62 |
| 5,601,982 A | 2/1997 | Sargent et al. | 435/6 |
| 5,605,662 A | 2/1997 | Heller | 422/68.1 |
| 5,605,798 A | 2/1997 | Köster | 435/6 |
| 5,607,912 A | 3/1997 | Samejima et al. | 510/411 |
| 5,609,907 A | 3/1997 | Natan | 427/2.12 |
| 5,622,824 A | 4/1997 | Köster | 435/6 |
| 5,631,134 A | 5/1997 | Cantor | 435/6 |
| 5,633,496 A | 5/1997 | Sakairi et al. | 250/288 |
| 5,635,713 A | 6/1997 | Labowsky | 250/282 |
| 5,643,800 A | 7/1997 | Tarantino et al. | 436/518 |
| 5,650,489 A | 7/1997 | Lam et al. | 530/334 |
| 5,654,150 A | 8/1997 | King et al. | 435/6 |
| 5,663,242 A | 9/1997 | Ghosh et al. | 525/329.4 |
| 5,665,967 A | 9/1997 | Coxon et al. | 250/287 |
| 5,670,322 A | 9/1997 | Eggers et al. | 435/6 |
| 5,670,381 A | 9/1997 | Jou et al. | 436/518 |
| 5,677,195 A | 10/1997 | Winkler et al. | 436/518 |
| 5,683,881 A | 11/1997 | Skiena et al. | 435/6 |
| 5,686,656 A | 11/1997 | Amirav et al. | 73/23.41 |
| 5,688,642 A | 11/1997 | Chrisey et al. | 435/6 |
| 5,691,141 A | 11/1997 | Köster | 435/6 |
| 5,693,463 A | 12/1997 | Edwards et al. | 435/6 |
| 5,700,642 A | 12/1997 | Monforte et al. | 435/6 |
| 5,710,028 A | 1/1998 | Eyal et al. | 435/91.1 |
| 5,716,780 A | 2/1998 | Edwards et al. | 435/6 |
| 5,716,825 A | 2/1998 | Hancock et al. | 435/286.5 |
| 5,723,320 A | 3/1998 | Dehlinger et al. | 435/91.1 |
| 5,726,014 A | 3/1998 | Edwards et al. | 435/6 |
| 5,738,990 A | 4/1998 | Edwards et al. | 435/6 |
| 5,743,960 A | 4/1998 | Tisone | 118/683 |
| 5,744,131 A | 4/1998 | Edwards et al. | 424/78.08 |
| 5,756,050 A | 5/1998 | Ershow et al. | 422/100 |
| 5,759,779 A | 6/1998 | Dehlinger et al. | 435/6 |
| 5,763,263 A | 6/1998 | Dehlinger et al. | 435/287 |
| 5,770,272 A | 6/1998 | Biemann et al. | 427/421 |
| 5,770,367 A | 6/1998 | Southern et al. | 435/6 |
| 5,770,860 A | 6/1998 | Franzen | 250/288 |
| 5,777,324 A | 7/1998 | Hillenkamp | 250/288 |
| 5,789,395 A | 8/1998 | Amin et al. | 514/152 |
| 5,798,210 A * | 8/1998 | Canard et al. | |
| 5,807,522 A | 9/1998 | Brown et al. | 422/50 |
| 5,828,063 A | 10/1998 | Köster et al. | 250/288 |
| 5,830,655 A | 11/1998 | Monforte et al. | 435/6 |
| 5,846,717 A | 12/1998 | Brow et al. | 435/6 |
| 5,851,765 A | 12/1998 | Köster | 435/6 |
| 5,853,989 A | 12/1998 | Jeffreys et al. | 435/6 |
| 5,854,486 A | 12/1998 | Dreyfus | 250/288 |
| 5,864,137 A | 1/1999 | Becker et al. | 250/287 |
| 5,869,240 A | 2/1999 | Patterson | 435/6 |
| 5,869,241 A | 2/1999 | Edwards et al. | 435/6 |
| 5,869,242 A | 2/1999 | Kamb | 435/6 |
| 5,872,003 A | 2/1999 | Köster | 435/283.1 |
| 5,872,010 A | 2/1999 | Karger et al. | 436/173 |
| 5,885,775 A | 3/1999 | Haff et al. | 435/6 |
| 5,885,841 A | 3/1999 | Higgs, Jr. et al. | 436/89 |
| 5,888,778 A * | 3/1999 | Shuber | |
| 5,888,819 A | 3/1999 | Goelet et al. | 435/5 |
| 5,900,481 A | 5/1999 | Lough et al. | 536/55.3 |
| 5,925,520 A | 7/1999 | Tully et al. | 435/6 |
| 5,927,547 A | 7/1999 | Papen et al. | 222/57 |
| 5,928,906 A | 7/1999 | Köster et al. | 435/91.2 |
| 5,928,952 A | 7/1999 | Hutchins et al. | 436/50 |
| 5,965,363 A | 10/1999 | Monforte et al. | 435/6 |
| 5,969,350 A | 10/1999 | Kerley et al. | 250/287 |
| 5,975,492 A | 11/1999 | Brenes | 251/175 |
| 5,976,798 A | 11/1999 | Parker et al. | 435/6 |
| 5,985,356 A | 11/1999 | Schultz et al. | 427/8 |
| 6,001,567 A | 12/1999 | Brow et al. | 435/6 |
| 6,004,744 A | 12/1999 | Goelet et al. | 435/5 |
| 6,006,171 A | 12/1999 | Vines et al. | 702/184 |
| 6,007,987 A | 12/1999 | Cantor et al. | 435/6 |
| 6,010,849 A | 1/2000 | Edwards et al. | 435/6 |
| 6,017,693 A | 1/2000 | Yates, III et al. | 435/5 |
| 6,022,688 A | 2/2000 | Jurinke et al. | 435/6 |
| 6,024,925 A | 2/2000 | Little et al. | 422/100 |
| 6,025,193 A | 2/2000 | Weiss | 435/320.1 |
| 6,027,890 A | 2/2000 | Ness et al. | 435/6 |
| 6,040,193 A | 3/2000 | Winkler et al. | 436/180 |
| 6,043,031 A | 3/2000 | Köster et al. | 435/6 |
| 6,051,378 A | 4/2000 | Monforte et al. | 435/6 |
| 6,060,022 A | 5/2000 | Pang et al. | 422/65 |
| 6,074,823 A | 6/2000 | Köster | 435/6 |
| 6,090,558 A | 7/2000 | Butler et al. | 435/6 |
| 6,104,028 A | 8/2000 | Hunter et al. | 250/288 |
| 6,110,426 A | 8/2000 | Shalon et al. | 422/68.1 |
| 6,111,251 A | 8/2000 | Hillenkamp | 250/288 |
| 6,121,048 A | 9/2000 | Zaffaroni et al. | 436/45 |
| 6,132,685 A | 10/2000 | Kercso et al. | 422/104 |
| 6,133,436 A | 10/2000 | Köster et al. | 536/24.3 |
| 6,136,269 A | 10/2000 | Winkler et al. | 422/61 |
| 6,140,045 A | 10/2000 | Wohlstadter et al. | 435/6 |
| 6,140,053 A | 10/2000 | Köster | 435/6 |
| 6,146,854 A | 11/2000 | Köster et al. | 435/1.1 |
| 6,147,344 A | 11/2000 | Annis et al. | 250/281 |
| 6,188,064 B1 | 2/2001 | Köster | 250/282 |
| 6,194,144 B1 | 2/2001 | Koster | 435/6 |
| 6,197,498 B1 | 3/2001 | Koster | 435/5 |
| 6,207,370 B1 | 3/2001 | Little et al. | 435/6 |
| 6,207,390 B1 | 3/2001 | Cantor et al. | 435/7.1 |
| 6,214,551 B1 | 4/2001 | Sanghvi et al. | 435/6 |
| 6,221,601 B1 | 4/2001 | Köster et al. | 435/6 |
| 6,221,605 B1 | 4/2001 | Köster | 435/6 |
| 6,225,061 B1 | 5/2001 | Becker et al. | 435/6 |
| 6,225,450 B1 | 5/2001 | Köster | 536/22.1 |
| 6,232,076 B1 * | 5/2001 | Schulz | |
| 6,235,478 B1 | 5/2001 | Köster | 435/6 |
| 6,238,871 B1 | 5/2001 | Köster | 435/6 |
| 6,258,538 B1 | 7/2001 | Köster et al. | 435/6 |
| 6,265,716 B1 | 7/2001 | Hunter et al. | 250/288 |
| 6,268,131 B1 | 7/2001 | Kang et al. | 435/6 |
| 6,268,144 B1 | 7/2001 | Köster | 435/6 |
| 6,270,835 B1 | 8/2001 | Hunt et al. | 427/79 |
| 6,277,573 B1 | 8/2001 | Köster | 435/6 |
| 6,284,497 B1 | 9/2001 | Sabanayagam et al. | 435/91.2 |
| 6,287,844 B1 | 9/2001 | Szafranski et al. | 435/252.33 |
| 6,300,076 B1 | 10/2001 | Köster | 435/6 |
| 6,303,309 B1 | 10/2001 | Jurinke et al. | 435/6 |
| 6,322,970 B1 | 11/2001 | Little et al. | 435/6 |

FOREIGN PATENT DOCUMENTS

| | | |
|---|---|---|
| DE | 4438630 | 5/1996 |
| DE | 19618032 | 5/1996 |
| DE | 19628178 | 7/1996 |
| DE | 19754978 | 12/1997 |
| DE | 19731479 | 8/1998 |
| EP | 0175467 | 3/1986 |
| EP | 0360676 | 3/1990 |
| EP | 0543550 | 5/1993 |
| EP | 0593789 | 4/1994 |
| EP | 0596205 | 5/1994 |
| EP | 0683234 | 11/1995 |
| EP | 0771019 | 5/1997 |
| EP | 0828855 | 12/1999 |
| FR | 2597260 | 5/1991 |
| FR | 2749662 | 11/1996 |
| GB | 2017105 | 3/1979 |
| GB | 2233654 | 1/1991 |
| GB | 2260811 | 4/1993 |
| GB | 2312782 | 11/1997 |
| GB | 2332273 | 6/1999 |
| JP | 63230086 | 9/1988 |
| JP | 2215399 | 8/1990 |
| JP | 4178359 | 6/1992 |
| WO | 8502907 | 7/1985 |
| WO | 8903432 | 4/1989 |
| WO | 8906700 | 7/1989 |
| WO | 8912624 | 12/1989 |
| WO | 8912694 | 12/1989 |
| WO | 9001564 | 2/1990 |
| WO | 9111533 | 1/1991 |
| WO | 9115600 | 10/1991 |
| WO | 9205287 | 4/1992 |
| WO | 9309668 | 5/1993 |
| WO | 9315407 | 8/1993 |
| WO | 9323563 | 11/1993 |
| WO | 9324834 | 12/1993 |
| WO | 9416101 | 7/1994 |
| WO | 9420978 | 9/1994 |
| WO | 9421822 | 9/1994 |
| WO | 9428418 | 12/1994 |
| WO | 9507361 | 3/1995 |
| WO | 9513381 | 5/1995 |
| WO | 9513538 | 5/1995 |
| WO | 9515400 | 6/1995 |
| WO | 9504160 | 9/1995 |
| WO | 9525737 | 9/1995 |
| WO | 9427719 | 11/1995 |
| WO | 9531429 | 11/1995 |
| WO | 9535505 | 12/1995 |
| WO | 9610648 | 4/1996 |
| WO | 9614406 | 5/1996 |
| WO | 9615262 | 5/1996 |
| WO | 9617080 | 6/1996 |
| WO | 9621042 | 7/1996 |
| WO | 9629431 | 9/1996 |
| WO | 9630545 | 10/1996 |
| WO | 9632504 | 10/1996 |
| WO | 9636987 | 11/1996 |
| WO | 9637630 | 11/1996 |
| WO | 9708306 | 3/1997 |
| WO | 9719110 | 5/1997 |
| WO | 9733000 | 9/1997 |
| WO | 9737041 | 10/1997 |
| WO | 9740462 | 10/1997 |
| WO | 9742348 | 11/1997 |
| WO | 9743617 | 11/1997 |
| WO | 9803257 | 1/1998 |
| WO | 9811249 | 3/1998 |
| WO | 9812355 | 3/1998 |
| WO | 9812734 | 3/1998 |
| WO | 9814982 | 4/1998 |
| WO | 9820019 | 5/1998 |
| WO | 9820020 | 5/1998 |
| WO | 9820166 | 5/1998 |
| WO | 9823284 | 6/1998 |
| WO | 9826095 | 6/1998 |
| WO | 9833052 | 7/1998 |
| WO | 9833808 | 8/1998 |
| WO | 9835609 | 8/1998 |
| WO | 9824935 | 11/1998 |
| WO | 9854751 | 12/1998 |
| WO | 9905323 | 2/1999 |
| WO | 9912040 | 3/1999 |
| WO | 9914362 | 3/1999 |
| WO | 9931273 | 6/1999 |
| WO | 9931278 | 6/1999 |
| WO | 9955718 | 11/1999 |
| WO | 9957318 | 11/1999 |
| WO | 0051053 | 8/2000 |
| WO | 0056446 | 9/2000 |
| WO | 0060361 | 10/2000 |
| WO | 0196607 | 12/2001 |

OTHER PUBLICATIONS

Khrapko et al., "An oligonucleotide hybridization approach to DNA sequencing," *FEBS Letters* 256(1,2): 118–122 (1989).

Maskos, U. and E.M. Southern, "Oligonucleotide hybridisations on glass supports: an novel linker for oligonucleotide synthesis and hybridisation properties of oligonucleotides synthesised in situ," *Nucleic Acids Research* 20(7): 1679–1684 (1992).

Aberth et al., "Secondary Ion Mass Spectrometry with Cesium Ion Primary Beam and Liquid Target Matrix for Analysis of Bioorganic Compounds", *Anal. Chem.* 54:2029–2034 (1982).

Adler et al., "Cell Membrane Coating with Glutaraldehyde: Application to a Versatile Solid–Phase Assay for Thyroid Membrane Proteins and Molecules Interacting with Thyroid Membranes", *Anal. Biochem.*, 148:320–327 (1985).

Bai et al., "Matrix–assisted Laser Desorption/Ionization Mass Spectrometry of Restriction Enzyme–digested Plasmid DNA Using an Active Nafion Substrate", *Rapid Comm. Mass Spec.* 8:687–691 (1994).

Bains et al., "A Novel Method For Nucleic Acid Sequence Determination", *J. Theor Biol.*, 135:303–307 (1988).

Bannwarth, W., "Solid–Phase Synthesis of Oligodeoxynucleotides Containing Phosphoramidate Internucleotide Linkages and their Specific Chemical Cleavage", *Helvetica Chimica Acta*, 71:1517–1527, (1988).

Batista–Viera et al., "A New Method for Reversible Immobilization of Thiol Biomolecules Based on Solid–Phase Bound Thiolsulfonate Groups", *App. Biochem. Biotech.*, 31:175–195 (1991).

Belanger et al., "Molecular Mass and Carbohydrate Structure of Prostate Specific Antigen: Studies for Establishment of an International PSA Standard", *Prostate* 27(4):187–197 (1995).

Benner et al., "DNA Base–Pair Substitutions Detected in Double–Stranded DNA with Matrix–Assisted Laser Desorption/Ionization Time–of–Flight Mass Spectrometry", *Eur. Mass Spectrom.*, 1:479–485 (1995).

Berkenkamp et al., "Performance of Infrared Matrix–assisted Laser Desorption/Ionization Mass Spectrometry with Lasers Emitting in the 3 $\mu$m Wavelength Range", *Rapid Comm. Mass Spec.*, 11:1399–1406 (1997).

Börnsen et al., "Influence of Solvents and Detergents on Matrix–assisted Laser Desorption/Ionization Mass Spectrometry Measurements of Proteins and Oligonucleotides", *Rapid Comm. Mass Spec.*, 11:603–609 (1997).

Broccoli et al., "Telomerase Activity in Normal and Malignant Hematopoietic Cells", *Proc. Nat'l. Acad. Sci. U.S.A.*, 92:9082–9086 (1995).

Broude et al., "Enhanced DNA Sequencing By Hybridization", *Proc. Natl. Acad. Sci. USA*, 91:3072–3076 (1994).

Brown et al., "Mass Resolution Improvement by Incorporation of Pulsed Ion Extraction in a Matrix–Assisted Laser Desorption/Ionization Linear Time–of–Flight Mass Spectrometer", *Anal. Chem.*, 67:1998–2003 (1995).

Burlingame et al., "Mass Spectrometry", *Anal. Chem.*, 70:647R–716R (1998).

Busch et al., "Mass Spectrometry of Large, Fragile, and Involatile Molecules", *Science*, 218:247–254 (1982).

Certified English translation of the Russian article: Elov et al. "RNA Synthesis by Use of T7 RNA Polymerase and Immobilized DNA in a Flowing–type Reactor", *Bioorganicheskaya Khimiya* 17(6):789–794 (1999).

Certified English translation of the French Patent Application FR 2597260, "A process for automatic direct introduction of samples into a mass spectrometer and a device for implementing this process."

Certified English translation of the PCT Patent Application WO 98/03257, "Solid supports for analytical measurement methods, their production and their use."

Certified English translation of the German Patent Application DE 3221681, "Mass spectrometer with an external sample holder."

Chait et al., "Weighing Naked Proteins: Practical, High–Accuracy Mass Measurement of Peptides and Proteins", *Science*, 257:1885–1894 (1992).

Chan et al., "OMS Letters", *Org. Mass Spec.*, 27:53–56 (1992).

Ch'ang et al., "Detection of ΔF508 Mutation of the Cystic Fibrosis Gene by Matrix–assisted Laser Desorption/Ionization Mass Spectrometry", *Rapid Comm. in Mass Spectrom.*, 9:772–774 (1995).

Chee et al., "Accessing Genetic Information with HighDensity DNA Arrays", *Science*, 274:610 (1996).

Chee, "Enzymatic Multiplex DNA Sequencing," *Nucl. Acids Res.* 19(12):3301–3305 (1991).

Chen et al., "Stable–Isotope–Assisted MALDI–TOF Mass Spectrometry for Accurate Determination of Nucleotide Compositions of PCR Products", *Anal. Chem.* 71(15):3118–3125 (1999).

Church et al., "Multiplex DNA Sequencing," *Science*, 240:185–188 (1988).

Collins et al., "A DNA Polymorphism Discovery Resource for Research on Human Genetic Variation", *Genome Res.*, 8:1229–1231 (1998).

Cornett et al., "Liquid Mixtures for Matrix–Assisted Laser Desorption", *Anal. Chem.*, 65:2608–2613 (1993).

Cosstick et al., "Synthesis and Properties of Dithymidine Phosphate Analogues Containing 3'–thiothymidine", *Nucl. Acid Res.*, 18:829–835 (1990).

Crain et al., "Applications of Mass Spectrometry to the Characterization of Oligonucleotides and Nucleic Acids", *Curr. Opin. Biotech.*, 9:25–34 (1998).

Dale et al., "Graphite/Liquid Mixed Matrices for Laser Desorption/Ionization Mass Spectrometry", *Anal. Chem.*, 68:3321–3329 (1996).

Dass et al., "Particle Beam Induced Reactions between Peptides and Liquid Matrices", *Anal. Chem.*, 60:2723–2729 (1988).

Derwent# 007678032, WPI Acc No. 88–311964/198844, citing Japanese Patent Application JP 63230086 A, "Carrier immobilising physiological active substance—comprises binding chain–form disulphide cpd. via epoxy gp. with latex contg. polymer particles."

Derwent# 008221915, WPI Acc. No. 90–108916/199015, citing European Patent Application EP 0360676 A, "Size analysis of biological mol. fragments—by mass spectrometry, esp. in nucleic acid sequencing."

Derwent# 008415766, WPI Acc. No. 90–302767/199040, citing Japanese Patent No. JP 2215399 A, "Method for detecting DNA—includes denaturing to single strand, combining with DNA primer having corresp. base sequence forming replicator etc."

Derwent# 009135586, WPI Acc No. 1992–263024, citing Japanese Patent JP 4178359 A, "New anti–inflammatory tetracycline derivs.—for treating articular rheumatism, osteoarthritis, Reiter's syndrome, Lyme disease, etc."

Derwent# 010222178, WPI Acc. No. 95–123433/199516, citing PCT Patent Application WO 9507361 A, "Detecting presence and position of mutation(s) in double stranded DNA—by amplification, labelling strands with different markers, hybridisation and detecting heteroduplex by cleavage of unpaired strands."

Derwent# 010643408, WPI Acc. No. 1996–140362/199615, citing German Patent DE 4431174 A, "Detecting tumour specific mRNA by conversion to cDNA and amplification—provides early, sensitive and specific diagnosis and monitoring, partic. by analysis of blood or sputum."

Derwent# 010725941, WPI Acc. No. 1996–222896/199623, citing German Patent No. DE 4438630 A, "Amplification of non–characterized DNA fragments—using only a single primer, with formation of hairpin loops during a second strand synthesis."

Derwent# 011458787, WPI Acc. No. 1997–436694/199741, citing German Patent No. DE 19628178 C, "Loading matrix–assisted laser desorption–ionisation sample plate for mass spectrometric analysis—using simple multi–pipette to prepare tens of thousands of samples rapidly and reliably for e.g. biochemical and genetic investigations optionally using electrophoretic concentration and delivery technique."

Derwent# 011635345, WPI Acc. No. 1998–052473/199805, citing French Patent No. FR 2749662 A, "Automatic laboratory for analysing samples—has robot and analysers in one chamber connected by sample transfer conveyors to second chamber with human operator access."

Derwent# 012012061, WPI Acc. No. 1998–428971/199837, citing German Patent No. DE 19731479 A, "Device for analysis of target chemcicals has light emitting array—with chemical binder elements attached to capture target chemicals which change emitted light pattern accordingly."

Drmanac et al., "DNA Sequence Determination by Hybridization: A Strategy For Efficient Large–Scale Sequencing", *Science*, 260:1649–1652 (1993).

Drmanac et al., "Sequence Of Megabase Plus DNA By Hybridization: Theory Of The Method", *Genomics*, 4:114–128 (1989).

Duchateau et al., "Selection of buffers and of an ion–pairing agent for thermospray liquid chromatographic—mass spectrometric analysis of ionic compounds", *J. Chromatogr*, 552:605–612 (1991).

Eckstein, F., (Ed.). "Oligonucleotides and Analogues: A Practical Approach", *Oxford University Press*, 56–57, 137–139, 256–259, (1991).

Elov et al., "Synthesis of RNA using T7 RNA polymerase and immobilized DNA in a stream type reactor", *Bioorganicheskaia Khimiia*, 17(6):789–794 (1999).

Fabris et al., "Massive Cluster Impact Ionization on a Four Sector Tandem Mass Spectrometer", *J. Mass Spec.*, 30:140–143 (1995).

Feng et al., "The RNA Component of Human Telomerase", *Science*, 269(5228):1236–1241 (1995).

Foster, et al., "Naming Names in Human Genetic Variation Research", *Genome Res.*, 8:755–757 (1998).

Frohman, M., "Cloning PCR Products" Chapter 12 in *The Polymerase Chain Reaction*, Mullis et al., (Eds.), Birkhauser, Boston, pp. 14–37 (1994).

George et al., "Current Methods in Sequence Comparison and Analysis," Chapter 12 of: Macromolecular Sequencing and Synthesis, *Selected Methods and Applications*, Schlesinger (Ed.), 127–149 (1988).

Grotjahn, L., "Oligonucleotides Sputtering from Liquid Matrices", *Springer Proc. Phys.*, 9:118–125 (1986).

Grotjahn, L., "Sequencing of Oligodoxyribonucleotides by Negative FAB–MS", *Int. J. Mass Spec. Ion Phys.*, 46:439–442 (1983).

Haag et al., "Rapid Identification and Speciation of Haemophilus Bacteria by Matrix–assisted Laser Desorption/Ionization Time–of–Flight Mass Spectrometry", *J. Mass Spec.*, 33(8):750–756 (1998).

Hacia et al., "Detection of Heterozygous Mutations in BRCA1 Using High Density Oligonucleotide Arrays and Two–Colour Fluorescence Analysis", *Nature Genetics*, 14:441–447 (1996).

Harada et al., "Diethanolamine Assisted Secondary Ion Mass Spectrometry of Natually Occurring Complex Oligosaccharides", *Org. Mass Spec.*, 17(8):386–391 (1982).

Herpich et al., "HPLC of Nucleic Acid Components with Volatile Mobile Phases 1. Fast Nucleotide Separators Using Ammonium Carbonate and Ammonium Bicarbonate Gradients", *J. High Resolut. Chromatogr.*, 15:41–42 (1992).

Hinton et al., "The Application of Robotics to Fluorometric and Isotopic Analyses of Uranium", *Chemometrics and Intelligent Laboratory Systems: Laboratory Info. Management*, 21:223–227 (1993).

Hunter et al., "Frozen–solution MALDI Mass Spectrometry Studies of DNA", *Proc SPIE–Int Soc. Opt. Eng.*, 2680:384–389 (1996).

Jacobson et al., "Applications of Mass Spectrometry to DNA Sequencing", *GATA*, 8(8):223–229 (1991).

Ji et al., "Two–dimensional Electrophoretic Analysis of Proteins Expressed by Normal and Cancerous Human Crypts: Application of Mass Spectrometry to Peptide–mass Fingerprinting", *Electrophoresis*, 15:391–405 (1994).

Jiang et al., "The Liquid Matrix Effects for Determining Ionization of Oligonucleotides by LSIMS", *Chin Sci. Bull.*, 37(17):1431–1435 (1992).

Jonkman et al., "Low–temperature Positive Secondary Ion Mass Spectrometry of Neat and Argon–Diluted Organic Solids", *Anal. Chem.*, 50(14):2078–2082 (1978).

Kambara, H., "Characteristics of Molecular Secondary Ion Mass Spectrometry", *Springer Ser. Chem. Phys.*, 36:357–362 (1984).

Khrapko et al., "A Method for DNA Sequencing by Hybridization with Oligonucleotide Matrix", *J. DNA Sequencing and Mapping*, 1:375–388 (1991).

Kim et al., "Investigation of Porphyrins and Metalloporphyrins by Liquid Matrix–assisted Laser Desorption Mass Spectrometry", *Mikrochim Acta*, 113:101–111 (1994).

Kirpekar, et al., "DNA Sequence Analysis by MALDI Mass Spectrometry", *Nuclei Acids Res.*, 26(11):2554–2559 (1998).

Kolli et al., "A New Matrix for Matrix–assisted Laser Desorption/Ionization of Magnetic Sector Instruments with Point Detectors", *Rapid Comm. Mass Spec.*, 10:923–926 (1996).

Köster et al., "A Strategy for Rapid and Efficient DNA Sequencing by Mass Spectrometry", *Nat. Biotechnol.*, 14:1123–1128 (1996).

Köster et al., "Oligonucleotide Synthesis and Multiplex DNA Sequencing Using Chemiluminescent Detection," *Nucl. Acids Res., Symposium Series*, 24:318–321 (1991).

Kovacik et al., "Liquid Secondary Ion Mass Spectrometry of Methyl Glycosides of Oligosaccharides Using Matrices Containing Carboxamides", *Rapid Comm. Mass Spec.*, 10:166–1667 (1996).

Krishnamurthy et al., "Rapid Identification of Bacteria by Direct Matrix–assisted Laser Desorption/Ionization Mass Spectrometric Analysis of Whole Cells", *Rapid Comm. Mass Spec.*, 10:1992–1996 (1996).

Krishnamurthy et al., "Biomolecules and Mass Spectrometry", *J. of Natural Toxins*, 6(2):121–162 (1997).

Lagerstrom et al., "Capture PCR: Efficient Amplification of DNA Fragments Adjacent to a Known Sequence in Human and YAC DNA", *PCR Methods and applications*, 1:111–119 (1991).

Laramee et al., "Evidence for Radical Anion Formation During Liquid Secondary Ion Mass Spectrometry Analysis of Oligonucleotides and Synthetic Oligomeric Analogues: A Deconvolution Algorithm for Molecular Ion Region Clusters", *Anal. Chem.*, 61:2154–2160 (1989).

Leonard et al., "High–resolution Structure of Mutagenic Lesion in DNA," *Proc. Nat. Acad. Sci. Biochem.*, 87:9573–9576 (1990).

Li et al., "Pulsed Laser Desorption Method for Volatilizing Thermally Labile Molecules for Supersonic Jet Spectroscopy ", *Rev. Sci. Instrum.*, 59(4):557–561 (1988).

Li et al., "High–resolution MALDI Fourier Transform Mass Spectrometry of Oligonucleotides", *Anal . Chem.* 68(13):2090–2096 (1996).

Little et al., "Mass Spectrometry from Miniaturized Arrays for Full Comparative DNA Analysis", *Nat. Med.*, 3(12):1413–1416 (1997).

Liu et al., "Use of a Nitrocellulose Film Substrate in Matrix–Assisted Laser Desorption/Ionization Mass Spectrometry for DNA Mapping and Screening", *Anal. Chem.*, 67:3482–3490 (1995).

Loboda et al., "Extraction Pulse Generator for Time–offlight Mass Spectrometry", *Rev. Sci. Instrum.*, 66(9):4740–4741 (1995).

Lubman et al., "Linear Mass Reflection with a Laser Photoionization Source for Time–of–flight Mass Spectrometry", *Anal. Chem.*, 55:1437–1440 (1983).

Matthews et al., "Analytical Strategies for the Use of DNA Probes", *Anal. Biochem.*, 169:1–25 (1988).

Maxam et al., "A New Method for Sequencing DNA", *Proc. Natl. Acad. Sci. USA* 74(2):560–64 (1977).

missing author—"Mass Spectrometry Used to Find Mass of Large Intact Nucleic Acids", *Chem. Eng. News*, p. 55 (1998).

Mizusawa et al., "Improvement of the Dideoxy Chain Termination Method of DNA Sequencing by Use of Deoxy–7–deazaguanosine Triphosphate in Place of dGTP", *Nucl. Acids Res.*, 14(3):1319–1324 (1986).

Moalem et al., "Cluster formation in the Vapor Produced by laser Pulsing of the $Y_1Ba_2Cu_3O_7$ Superconducting Solid", *J. of Vac. Sci. Tech.*, 10(5):3292–3299 (1992).

Mosca et al., "Mass Spectrometry and DNA Analysis", *Hemoglobin*, 17(3):261–268 (1993).

Muddiman et al., "Length and Base Composition of PCR–Amplified Nucleic Acids Using Mass Measurements from Electrospray Ionization Mass Spectrometry", *Anal. Chem.*, 69(8):1543–1549 (1997).

Naito et al., "Detection of Tyrosine Hydroxylase mRNA and Minimal Neuroblastoma Cells by the Reverse Transcription-Polymerase Chain Reaction", *Eur. J. Cancer*, 27(6):762–765 (1991).

Nakayame et al., "Direct Sequencing of Polymerase Chain Reaction Amplified DNA Fragments Through the Incorporation of Deoxynucleoside α–Thiotriphosphates", *Nucl. Acids Res.*, 16(21):9947–9959 (1988).

Nelson et al., "Time–of–flight Mass Spectrometry of Nucleic Acids by Laser Ablation and Ionization from a Frozen Aqueous Matrix", *Rapid Comm. Mass Spec.*, 4(9):348–351 (1990).

Nelson et al., "The Accuracy of Quantification from 1D NMR Spectra Using the PIQABLE Algorithm", *J. Mag. Res.*, 84:95–109 (1989).

Nordhoff et al., "Comparison of IR– and UV–matrix–assisted Laser Desorption/Ionization Mass Spectrometry of Oligodeoxynucleotides", *Nuc. Acids Res.*, 21(13):2460–2465 (1993).

Nordhoff et al., "Ion Stability of Nucleic Acids in Infrared Matrix–assisted Laser Desorption/Ionization Mass Spectrometry", *Nuc. Acids Res.*, 21(15):3347–3357 (1993).

O'Donnell–Maloney et al., "The Development of Microfabricated Arrays for DNA Sequencing and Analysis", *TIBTECH*, 14:401–407 (1996).

Olsson et al., "Isolation and Characterization of a Tumor Necrosis Factor Binding Protein from Urine", *Eur. J. Haematol.*, 42:270–275 (1989).

Ordoukhanian et al., "Design and Synthesis of a Versatile Photocleavable DNA Building Block. Application to Phototriggered Hybridization", *J. Am. Chem. Soc.*, 117:9570–9571 (1995).

Orita et al., "Detection of Polymorphisms of Human DNA by Gel Electrophoresis as Single–Strand Conformation Polymorphisms", *Proc. Natl. Acad. Sci. USA*, 86:2766–2770, (1989).

Overberg et al., "Laser Desorption Mass Spectrometry. Part II Performance and Applications of Matrix–assisted Laser Desorption/Ionization of Large Biomolecules", *Mass Spect. Biol. Sci.*, pp. 181–197 (1992).

Palejwala et al., "Quantitative Multiplex Sequence Analysis of Mutational Hot Spots. Frequency and Specificity of Mutations Induced by a Site–Specific Ethenocytosine in M13 Viral DNA", *Biochem.*, 32:4105–4111 (1993).

Pasini et al., "RET Mutations in Human Disease", *Trends in Genetics*, 12(4):138–144 (1996).

Pevzner et al., "Rearrangements of DNA Sequences and SBH", *Computers Chem.*, 18(3):221–223 (1994).

Pevzner et al., "Towards DNA Sequencing Chips", In *19th Int Conf Mathematical Foundations of Computer Science*, Lecturer Notes in Computer Science, Springer–Verlag, Berlin, 841:143–158 (1994).

Polettini et al., "Fully–automated Systematic Toxicological Analysis of Drugs, Poisons, and Metabolites in Whole Blood, Urine, and Plasma by Gas Chromatography—Full Scan Mass Spectrometry", *J. Chromatography B*, 713(1):265–279 (1998).

Promé et al., "Use of Combined Mass Spectrometry Methods for the Characterization of a New Variant of Human Hemoglobin: The Double Mutant Hemoglobin Villeparisis β77(EF1) His→Tyr, β80(EF4) Asn→Ser", *J. Am. Chem. Soc. Mass Spect.*, 7:163–167 (1996).

Richterich et al., "Cytosine Specific DNA Sequencing with Hydrogen Peroxide", *Nucl. Acids Res.*, 23(23):4922–4923 (1995).

Ruckman et al., "Laser–induced Ion Mass Analysis: A Novel Technique for Solid–state Examination", *Vacuum*, 34(10/11):911–924 (1994).

Sadeghi et al., "Compact Tunable Cr:LiSAF for Infrared Matrix–assisted Laser Desorption/Ionization", *Rapid Comm. Mass Spec.*, 11:393–397 (1997).

Sarkar et al., "Human Genetic Bi–allelic Sequences (HGBASE), a Database of Intra–genic Polymorphisms", 93(5):693–694 (1998).

Schneider et al., "Increased Stability of Nucleic Acids Containing 7–deaza–guanosine and 7–deaza–adenosine may Enable Rapid DNA Sequencing by Matrix–assisted Laser Desorption Mass Spectrometry", *Nucleic Acids Res.*, 23(9):1570–1575 (1995).

Seckinger et al., "Purification and Biologic Characterization of a Specific Tumor Necrosis Factor α Inhibitor", *J. Biochem.*, 264(20):11966–11973 (1989).

Senko et al., "Automated Assignment of Charge States from Resolved Isotopic Peaks for Mutiply Charged Ions", *J. Am. Soc. Mass Spec.*, 6:52–56 (1995).

Siegel et al., "Calicheamicin Derivatives Conjugated to Monoclonal Antibodies: Determination of Loading Values and Distributions by Infrared and UV Matrix–assisted Laser Desorption/Ionization Mass Spectrometry and Electrospray Ionization Mass Spectrometry", *Anal. Chem.*, 69:2716–2726 (1997).

Siegert et al., "Matrix–assisted Laser Desorption/Ionization Time–of–flight Mass Spectrometry for the Detection of Polymerase Chain Reaction Products Containing 7–Deazapurine Moieties", *Anal. Biochem.*, 243:55–65 (1966).

Siuzdak, G., "The Emergence of Mass Spectrometry in Biochemical Research", *PNAS*, 91:11290–11297 (1994).

Southern et al., "Analyzing and Comparing Nucleic Acid Sequences by Hybridization to Arrays of Oligonucleotides: Evaluation Using Experimental Modes", *Genomics*, 13:1008–1017 (1992).

Stahl et al., "Solid Phase DNA Sequencing Using the Biotin–Avidin System", *Nucl. Acids Res.*, 16(7):3025–3039 (1988).

Stults et al., "Improved Electrospray Ionization of Synthetic Oligodeoxynucleotides", *Rapid Comm. Mass Spectrom.*, 5:359–363 (1991).

Syvanen et al., "Detection of Point Mutations by SolidPhase Methods", *Human Mutation*, 3:172–179 (1994).

Szybalski et al., "Universal Restriction Endonucleases: Designing Novel Cleavage Specificities by Combining Adapter Olideoxinucleotide and Enzyme Moieties", *Gene*, 40:169–173 (1985).

Takayama, M., "1,5 Pentamediol as a Matrix for Negative–ion Fast Atom Bombardment Mass Spectrometry", *Org. Mass Spec.*, 26:1123–1124 (1991).

Tammen et al., "Proteolytic Cleavage of Glucagon–like Peptide–1 by Pancreatic β Cells and by Fetal Calf Serum Analyzed by Mass Spectrometry", *J. Chrom. A.*, 852:285–295 (1999).

Tang et al., "Matrix–assisted Laser Desoroption/Ionization Mass Spectrometry of Immobilized Duplex DNA Probes", *Nucleic Acids Res.*, 23(16):3126–3131 (1995).

Tang et al., "Chip–based Genotyping by Mass Spectrometry," *Proc. Natl. Acad. Sci. USA*, 96:10016–10020 (1999).

Tang et al., "Matrix–assisted Laser Desorption/Ionization of Restriction Enzyme–digested DNA", *Rapid Comm. Mass Spec.*, 8:183–186 (1994).

Tas et al., "Characterization of Virus Infected Cell Cultures by Pyrolysis/Direct Chemical Ionization Mass Spectrometry", *Biomed and Environ Mass Spec.*, 18:757–760 (1989).

Thompson, J., "Fitting Robots with White Coats", *Lab. Auto. Info. Manag.*, 31:173–193 (1996).

Trainor, G., "DNA Sequencing, Automation, and the Human Genome", *Anal. Chem.*, 62:418–426 (1990).

Uhlmann et al., "Antisense Oligonucleotides: A New Therapeutic Principle", *Chemical Reviews,* 90(4):544–583 (1990).

Welham et al., "The Rapid Identification of Intact Microorganisms by Matrix–assisted Laser Desorption/Ionization Time–of–flight Mass Spectrometry", *Pharmacy and Pharmacology Comm.* 4:81–87 (1998).

Williams et al., "p–Nitroaniline/Glycerol: a Binary Liquid Matrix for Matrix–assisted Laser Desorption/Ionization Analysis", *Eur. Mass Spec.*, 4:379–383 (1998).

Wolter et al., "Influence of the Matrix on the Analysis of Small Oligoribonucleotides by Fast Atom Bombardment Mass Spectrometry", *J. Mass Spe.*, 30:485–491 (1995).

Wu et al., "The Ligation Amplification Reaction (LAR)— Amplification of Specific DNA Sequences Using Sequential Rounds of Template–Dependent Ligation", *Genomics*, 4:560–569 (1989).

Wu et al., "Time–of–Flight Mass Spectrometry of Underivatized Single–Stranded DNA Oligomers by Matrix–Assisted Laser Desorption", *Anal. Chem.*, 66:1637–1645 (1994).

Yau et al., "Threshold Fluences for Production of Positive and Negative Ions in Matrix–assisted Laser Desorption/Ionisation Using Liquid and Solid Matrices", *Chem. Phys. Lett.*, 202(1,2):93–100 (1993).

Yoshida et al., "Detection of High Mass Molecular Ions by Laser Desorption Time–of–flight Mass Spectrometry", *Shitsuryo Bunscki*, 36(2):59–69 (1988).

Youil et al., "Screening for Mutations by Enzyme Mismatch Cleavage with T4 Endonuclease VII", *Proc. Natl. Acad. Sci. USA*, 92:87–91 (1995).

Zuckermann et al., "Efficient Methods for Attachment of Thiol Specific Probes to the 3'–ends of Synthetic Oligodeoxyribonucleotides", *Nucl. Acids Res.*, 15(13):5305–5321 (1987).

Gross et al. "Matrix–assisted laser desorption/ionisation-–mass spectrometry applied to biological macromolecules" *Trends in Analytical Chem.* V 17(8–9) pp. 470–484 (1998).

Jacutin et al. "Test of the potential of a dATP surrogate for sequencing via MALDI–MS" *Nucleic Acid Research* V.25(24) pp. 5072–5076 (1997).

"Invitation To Pay Additional Fees" with Partial International Search Report for International Application PCT/US 01/19249, dated Nov. 11, 2002.

* cited by examiner

Figure 8

Base composition density distributions for
7-mers using different nucleotide sets.

i) 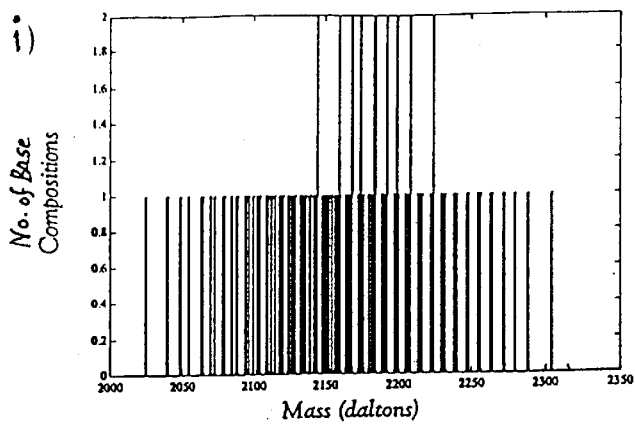

C = 289.2
T = 304.2
A = 313.2
G = 329.2

*Naturally Occurring Bases*
Peaks can be closer than one dalton.
Total No. of different base compositions = 120
Actual number of represented masses = 110
Avg. No. of compositions per mass value = 1.091 ii) 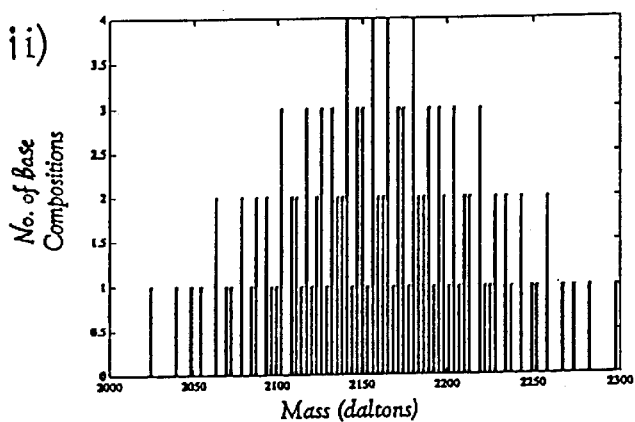

C = 289.2
T = 304.2
A = 313.2
G = 328.2

*Substitution with 7-deaza-dG*
Minimum peak separation = 3 daltons
Number of allowed mass values = 92
Actual number of represented masses = 64
Avg. No. of compositions per mass value = 1.875 iii) 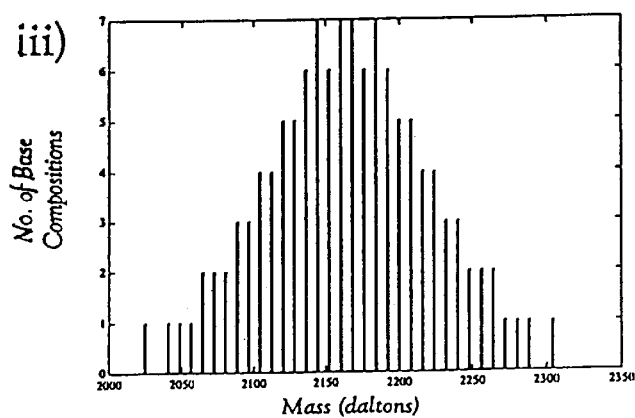

C = 289.2
T = 305.2
A = 313.2
G = 329.2

*Substitution with deutero-dT*
Minimum peak separation = 8 daltons
Number of allowed mass values = 36
Actual number of represented masses = 34
Avg. No. of compositions per mass value = 3.529

SEQUENCE LISTING

```
<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide target sequence

<400> SEQUENCE: 1
tgaatgtaga cctcacgt                                                 18
```

USE OF NUCLEOTIDE ANALOGS IN THE ANALYSIS OF OLIGONUCLEOTIDE MIXTURES AND IN HIGHLY MULTIPLEXED NUCLEIC ACID SEQUENCING

RELATED APPLICATIONS

For U.S. purposes for priority is claimed under 35 U.S.C. §119(e) to U.S. provisional application Ser. No. 60/211,356, filed Jun. 13, 2000, to Charles R. Cantor and Fouad A. Siddiqi, entitled USE OF NUCLEOTIDE ANALOGS IN THE ANALYSIS OF OLIGONUCLEOTIDE MIXTURES AND IN HIGHLY MULTIPLEXED NUCLEIC ACID SEQUENCING." For international purposes benefit of priority is claimed thereto. The subject matter of U.S. provisional application Ser. No. 60/211,356 is incorporated by reference in it entirety.

Subject matter described herein was developed under NSF Grant No. Ger-9452651. The Government can have certain rights therein.

FIELD OF THE INVENTION

This invention relates to methods, particularly mass spectrometric methods, for the analysis and sequencing of nucleic acid molecules.

DESCRIPTION OF THE BACKGROUND

Since the recognition of nucleic acid as the carrier of the genetic code, a great deal of interest has centered around determining the sequence of that code in the many forms in which it occurs. Two studies made the process of nucleic acid sequencing, at least with DNA, a common and relatively rapid procedure practiced in most laboratories. The first describes a process whereby terminally labeled DNA molecules are chemically cleaved at single base repetitions (A. M. Maxam and W. Gilbert, Proc. Natl. Acad. Sci. USA 74:560-64, 1977). Each base position in the nucleic acid sequence is then determined from the molecular weights of fragments produced by partial cleavage. Individual reactions were devised to cleave preferentially at guanine, at adenine, at cytosine and thymine, and at cytosine alone. When the products of these four reactions are resolved by molecular weight, using, for example, polyacrylamide gel electrophoresis, DNA sequences can be read from the pattern of fragments on the resolved gel.

In another method DNA is sequenced using a variation of the plus-minus method (Sanger et al. (1977) Proc. Natl. Acad. Sci. USA 74:5463-67, 1977). This procedure takes advantage of the chain terminating ability of dideoxynucleoside triphosphates (ddNTPs) and the ability of DNA polymerase to incorporate ddNTPs with nearly equal fidelity as the natural substrate of DNA polymerase, deoxynucleoside triphosphates (dNTPs). Briefly, a primer, usually an oligonucleotide, and a template DNA are incubated in the presence of a useful concentration of all four dNTPs plus a limited amount of a single ddNTP. The DNA polymerase occasionally incorporates a dideoxynucleotide that terminates chain extension. Because the dideoxynucleotide has no 3'-hydroxyl, the initiation point for the polymerase enzyme is lost. Polymerization produces a mixture of fragments of varied sizes, all having identical 3' termini. Fractionation of the mixture by, for example, polyacrylamide gel electrophoresis, produces a pattern that indicates the presence and position of each base in the nucleic acid. Reactions with each of the four ddNTPs permits the nucleic acid sequence to be read from a resolved gel.

These procedures are cumbersome and are limited to sequencing DNA. In addition, with conventional procedures, individual sequences are separated by, for example, electrophoresis using capillary or slab gels, which slow. Mass spectrometry has been adapted and used for sequencing and detection of nucleic acid molecules (see, e.g., U.S. Pat. Nos. 6,194,144; 6,225,450; 5,691,141; 5,547,835; 6,238,871; 5,605,798; 6,043,031; 6,197,498; 6,235,478; 6,221,601; 6,221,605). In particular, Matrix-Assisted Laser Desorption/Ionization (MALDI) and ElectroSpray Ionization (ESI), which allow intact ionization, detection and exact mass determination of large molecules, i.e. well exceeding 300 kDa in mass have been used for sequencing of nucleic acid molecules.

A further refinement in mass spectrometric analysis of high molecular weight molecules was the development of time of flight mass spectrometry (TOF-MS) with matrix-assisted laser desorption ionization (MALDI). This process involves placing the sample into a matrix that contains molecules that assist in the desorption process by absorbing energy at the frequency used to desorb the sample. Time of flight analysis uses the travel time or flight time of the various ionic species as an accurate indicator of molecular mass. Due to its speed and high resolution, time-of-flight mass spectrometry is well-suited to the task of short-range, i.e., less than 30 base sequencing of nucleic acids. Since each of the four naturally occurring nucleotide bases dC, dT, dA and dG, also referred to herein as C, T, A and G, in DNA has a different molecular weight, $M_C = 289.2$ $M_T = 304.2$ $M_A = 313.2$ $M_G = 329.2$, where $M_C$, $M_T$, $M_A$, $M_G$ are average molecular weights in daltons of the nucleotide bases deoxycytidine, thymidine, deoxyadenosine, and deoxyguanosine, respectively, it is possible to read an entire sequence in a single mass spectrum. If a single spectrum is used to analyze the products of a conventional Sanger sequencing reaction, where chain termination is achieved at every base position by the incorporation of dideoxynucleotides, a base sequence can be determined by calculation of the mass differences between adjacent peaks. In addition, the method can be used to determine the masses, lengths and base compositions of mixtures of oligonucleotides and to detect target oligonucleotides based upon molecular weight.

MALDI-TOF mass spectrometry for sequencing DNA using mass modification (see, e.g., U.S. Pat. Nos. 5,547,835, 6,194,144; 6,225,450; 5,691,141 and 6,238,871) to increase mass resolution is available. The methods employ conventional Sanger sequencing reactions with each of the four dideoxynucleotides. In addition, for example for multiplexing, two of the four natural bases are replaced; dG is substituted with 7-deaza-dG and dA with 7-deaza-dA.

A variety of techniques and combinations thereof have been directed to improving the level of accuracy in determining the nucleotide compositions of mixtures of oligonucleotides using mass spectrometry, and many of these methods employ nucleotide analogs. For example, Muddiman et al. (Anal. Chem., 69(8): 1543–1549, 1997) discusses an algorithm for the unique definition of the base composition of PCR-amplified products, especially longer (>100 bp) oligonucleotides. The algorithm places a constraint on the otherwise large number of possible base compositions for long oligonucleotides by taking into account only those masses (measured by electrospray ionization mass spectrometry) that are consistent with that of their denatured complementary strands, assuming Watson-Crick base-pairing. In addition, the algorithm imposes the constraint of known primer compositions, since the primer sequences are known, and this constraint becomes especially significant with shorter PCR products whose mass of "unknown" sequence relative to that of the primer mass is small. Muddiman et al. also discusses invoking additional measurements for defining the base composition with even greater accuracy. These include the possibility of post-modifying the PCR product using e.g., dimethyl sulfate to selectively methylate every "G" in the PCR product, or using a modified base during PCR amplification, conducting mass measurements on the modified oligonucleotides, and comparing the mass measurements with those of the unmodified complementary strands.

Chen et al. (*Anal. Chem.,* 71(15): 3118–3125, 1999) reports a method that combines stable isotope $^{13}C/^{15}N$ labelling of PCR products with analysis of the mass shifts by MALDI-TOF mass spectrometry. The mass shift due to labelling of a single type of nucleotide (i.e, A, T, G or C) reveals the number of that type of nucleotide in a given fragment. While the method is useful in the measurement and comparison of nucleotide compositions of homologous sequences for sequence validation and in scoring polymorphisms, tedious repetitive sequencing reactions (using the four different labelled nucleotides) and mass spectrometric measurements are required.

Hence there is a need in the art for methods that (i) unambiguously assign nucleotides in a sequence, and, (ii) resolve large numbers of oligonucleotides that have the same length, different base compositions, and nearly equal (i.e., less than or equal to about 1 dalton difference) molecular weights. Therefore it is an object herein to provide methods that solve such problems

SUMMARY OF THE INVENTION

Provided herein are methods for sequencing and detecting nucleic acids using techniques, such as mass spectrometry and gel electrophoresis, that are based upon molecular mass. The methods use deoxynucleotide analogs, modified nucleotide terminators and/or mass-labeled primers in one or more reactions for sequencing or detection protocols that involve primer extension, and analyze these products from more than one oligonucleotide on, for example, a single mass spectrum. This provides a means for accurate detection and/or sequencing of a an oligonucleotide and is particularly advantageous for detecting or sequencing a plurality target nucleic acid molecules in a single reaction using any technique that distinguishes products based upon molecular weight. The methods herein are particularly adapted for mass spectrometric analyses.

For example, a sequencing method provided herein uses deoxynucleotide analogs, modified nucleotide terminators and/or mass-labeled primers in one or more Sanger sequencing reactions, and analyzes these products from more than one oligonucleotide on a single mass spectrum. In particular, a plurality of primers can be used to simultaneously sequence a plurality of nucleic acid molecules or portions of the same molecule. By extending the primers with mass-matched nucleotides, the resulting products mass shifts that are periodically related to the size of the original primer.

As a result, the sequence of any given oligonucleotide can be determined with a high level of accuracy, and also mixtures of a number of sequences can be multiplexed in a single mass spectrum. The limit on the number of oligonucleotides that can be sequenced simultaneously is governed by the base periodicity, the maximum mass shift, and the resolving power of analytical tool, such as the mass spectrometer. The base periodicity and maximum mass shift can be carefully engineered for optimal resolution and accuracy, depending on the number of sequences to be simultaneously analyzed, and the information desired; as many sequences as desired can be sequenced simultaneously especially in the detection and scoring of single nucleotide polymorphisms, insertions, deletions and other mutations.

In another embodiment, a target nucleic acid molecule is sequenced using mass-matched nucleotides and chain terminating nucleotides. For example, a primer is annealed to a target nucleic acid, the primer is extended in the presence of chain-terminating nucleotides and mass-matched nucleotides to produce extension products, the masses of the extension products follow a periodic distribution that is determined by the mass of the mass-matched nucleotides, and the sequence of the target nucleic acid is determined from the mass shift of each extension product from its corresponding periodic reference mass by virtue of incorporation of the chain terminator. The mass-matched nucleotides all have identical masses, and each chain terminating nucleotide has a distinct mass that differs from that of the other chain terminating nucleotides. This results in unique predetermined values of mass shift corresponding to each chain terminating nucleotide and based upon the original primer.

This method is adaptable for any sequencing method or detection method that relies upon or includes chain extension. These methods include, but are not limited to, sequencing methods based upon Sanger sequencing, and detection methods, such as primer oligo base extension (PROBE) (see, e.g., U.S. Pat. No. 6,043,031; allowed U.S. application Ser. No. 09/287,679; and U.S. Pat. No. 6,235,478), that rely include a step of chain extension.

Also, contemplated are methods, such as haplotyping methods, in which two mutations in the same gene are detection are provided. A detector (primer) oligonucleotide is to the hybridized to the first mutation and the primer is extended with mass-matched nucleotides and appropriately selected chain terminator(s) to detect the second mutation.

In other embodiments, a plurality of target nucleic acids can be multiplexed in a single reaction measurement by annealing each target nucleic acid to a primer of distinct molecular weight each primer is then extended with mass-matched nucleotides and chain terminators in formats that depend upon whether detection or sequencing is desired. These methods are particularly useful for methods of detection in which a primer is hybridized to a plurality of target nucleic acid molecules, such as immobilized nucleic acid molecules, hybrids separated from unhybridized nucleic acids and the detectors detected. Such methods include PROBE, in which case the extension reaction is performed in the presence chain terminators and mass matched deoxynucleotides.

The primers of distinct molecular weight can be selected to differ in molecular weight by a value that is greater than the maximum mass shift, i.e., the difference in molecular weight between the heaviest and the lightest nucleotide terminators in chain extension reactions. The difference in molecular weight between the primers for a plurality of target nucleic acids can be selected to be least 20 daltons greater than the maximum mass shift to account for the finite band width of the peaks.

The number of molecules that can be multiplexed is governed by the periodicity, the maximum mass shift, and the resolving power of the sequence detection instrument. In some embodiments, about 7 to about 25 or more molecules can be multiplexed. For scoring single nucleotide polymorphisms, only a single nucleotide terminator is required (depending on the base identity of the single nucleotide polymorphism). In this case, the maximum mass shift required is identically zero, so that larger numbers of molecules, greater than 25, 35, 50 and more, can be multiplexed, depending on the resolving power of the sequencing format, and for mass spectrometry the instrument. Depending on the amount of sequence information desired, one, two or three rather than four types of nucleotide terminators (corresponding to each of the four nucleic acid bases) can be used.

In other embodiments, the mass shift is obtained using pair-matched nucleotides, i.e., the mass of each nucleotide base-pair is selected so that the masses of all pairs are identical. In one embodiment thereof, the following steps are performed: (i) the target nucleic acid is copied or amplified by a method such as PCR in the presence of the pair-matched nucleotide set prior to the sequencing or detection reaction; (ii) the target nucleic acid is denatured, and a partially duplex hairpin primer is annealed and ligated to the single-stranded template; (iii) the primer is extended in the presence of chain terminating nucleotides and pair-matched nucleotides to produce extension products, where the masses of the extension products follow a periodic distribution that is determined by the mass of the pair-matched nucleotide set, and, (iv) the target nucleic acid is detected by virtue of its molecular weight or its sequence is determined from the mass shift of each extension product from its corresponding periodic reference mass.

In another embodiment, the mass of each terminating base pair is unique and resolvable, so that the mass shifts corresponding to each terminating base pair are unique. The nucleotide terminators are optionally mass-matched or can be of distinct masses as long as distinct values of mass shift are obtained for each terminating base pair.

In another embodiment, the extension products are treated to produce blunt-ended double-stranded extension products by methods known to those of skill in the art, such as the use of single-strand specific nucleases. In an aspect of this embodiment, a plurality of target nucleic acids can be multiplexed in a single reaction by annealing each target nucleic acid to a primer of distinct molecular weight. The primers can be selected to differ in molecular weight by a value that is greater than the maximum mass shift, i.e., the difference in molecular weight between the heaviest and the lightest nucleotide terminating base pairs. Since double stranded nucleic acid can be analyzed, the effective sequence read is halved relative to the embodiment employing mass-matched nucleotides, but the number of molecules that can be multiplexed is doubled, due to the increase in period (the value of the mass of a base pair, rather than a single mass-matched nucleotide). In exemplary embodiments, about 14 to about 50 sequences are multiplexed. In detection embodiments, about 50 or more molecules can be simultaneously multiplexed since only a single terminating base pair is added in the extension reaction.

In another embodiment, the chain termination reactions are carried out separately using a standard nucleotide terminator, pair-matched nucleotides, and mass-labeled primers, if modified nucleotide terminators which are either mass-matched or provide distinct values of mass shift for each terminating base pair are not available. The reactions are pooled prior to detection or sequence analysis. In one embodiment, the mass-labeled primers can have distinct values of molecular weight that give rise to unique values of mass shift or positional mass difference for each terminating base.

In andother method provided herein, a population of nucleic acids having the same length but different base compositions can be resolved by synthesizing the nucleic acids in the presence of a nucleotide analog to produce synthesized nucleic acids having incorporated the nucleotide analog, where the nucleotide analog is selected to optimally separate the masses of the population of nucleic acids according to their individual base compositions. For example, the nucleotide analog or analogs are selected to separate the population of nucleic acids according to base composition by greater than 1 dalton. In another embodiment, the nucleotide analog or analogs are selected to separate the population of nucleic acids according to base composition by mass values of about 3 daltons to about 8 daltons, depending on the choice of analog and on the resolving power of the detection instrument. In other embodiments, the nucleotide analog or analogs can be selected to restrict oligonucleotides having the same length to have the same mass, i.e., a peak separation of zero, regardless of differences in base composition, such as in detection methods, where it is desirable to separate populations of oligonucleotides according to their length.

Nucleic acid molecules that contain mass-matched nucleotides and/or pair-matched nucleotides are provided.

Also provided are combinations for practicing the methods provided herein. For instance, in one embodiment, the combinations include a set of mass-matched deoxynucleotides. In another embodiment, the combinations a set of pair-matched nucleotides and a set of mass-matched chain terminating nucleotides. In another embodiment, the combination includes a set of pair-matched nucleotides and chain terminating nucleotides which form terminating base pairs of distinctly different molecular weight. In yet another embodiment, the combination includes a set of pair-matched nucleotides and mass-labeled primers. In other embodiments, mass-staggered primers can be added to as optional components.

Kits containing the combinations with optional instructions and/or additional reagents are also provided. The kits contain the reagents as described herein and optionally any other reagents required to perform the reactions. Such reagents and compositions are packaged in standard packaging known to those of skill in the art. Additional vials, containers, pipets, syringes and other products for sequencing can also be included. Instructions for performing the reactions can be included.

Also provided herein are methods for optimization of the analysis of base compositions of mixtures of oligonucleotides by mass spectrometry. A single spectrum can be used to resolve a very large number of oligonucleotides having the same length but different molecular weights by incorporating a nucleotide analog into the oligonucleotides in the mixture such that the peaks are no closer than a minimum value called peak separation. The peak separation can be tailored by careful selection of the nucleotide analog and of a mass spectrometer with the desired resolving power.

The methods herein permit unambiguous and accurate analysis of the sequences or molecular weights of large numbers of oligonucleotides in a single mass spectrum by combining the rapidity of mass spectrometry with the resolving power of nucleotide analogs which are carefully selected and incorporated into the oligonucleotide mixture according to the desired application.

Other features and advantages will be apparent from the following detailed description and claims.

BRIEF DESCRIPTION OF THE FIGURES

FIG. 2a is a simulated mass spectrum showing the products and molecular masses of a reaction carried out with a suitable polymerase in the presence of a mass-matched nucleotide set ("dN") and the four standard dideoxynucleotide terminators. The base periodicity is the mass of dN, or 310 daltons. FIG. 2b shows a target second sequence resolved on the same mass spectrum shown in FIG. 2a, using a primer heavier by 77 daltons. The peaks corresponding to the reaction products from the first target sequence can fall within the spectrum in FIG. 2b, which can never intersect peaks from the second target sequence. This permits unambiguous resolution of both sequences each peak can be uniquely assigned to a nucleotide, a base position, and a target sequence.

FIG. 6b is a simulated mass spectrum of all reaction products shown in FIG. 6a. FIG. 6c is a graph representing the valid sequence permutations that can be elucidated from the mass spectrum shown in FIG. 6b. Boxed values are fragment masses, solid arrows show valid sequence branches, dashed arrows represent spurious branches. In practice valid branches are indistinguishable from spurious ones. FIG. 6d is a set of sequences consistent with the graph shown in FIG. 6c. Spurious sequence reconstructions are shown in lowercase letters, valid ones in uppercase letters.

DETAILED DESCRIPTION OF THE INVENTION

Definitions

Figure 1:
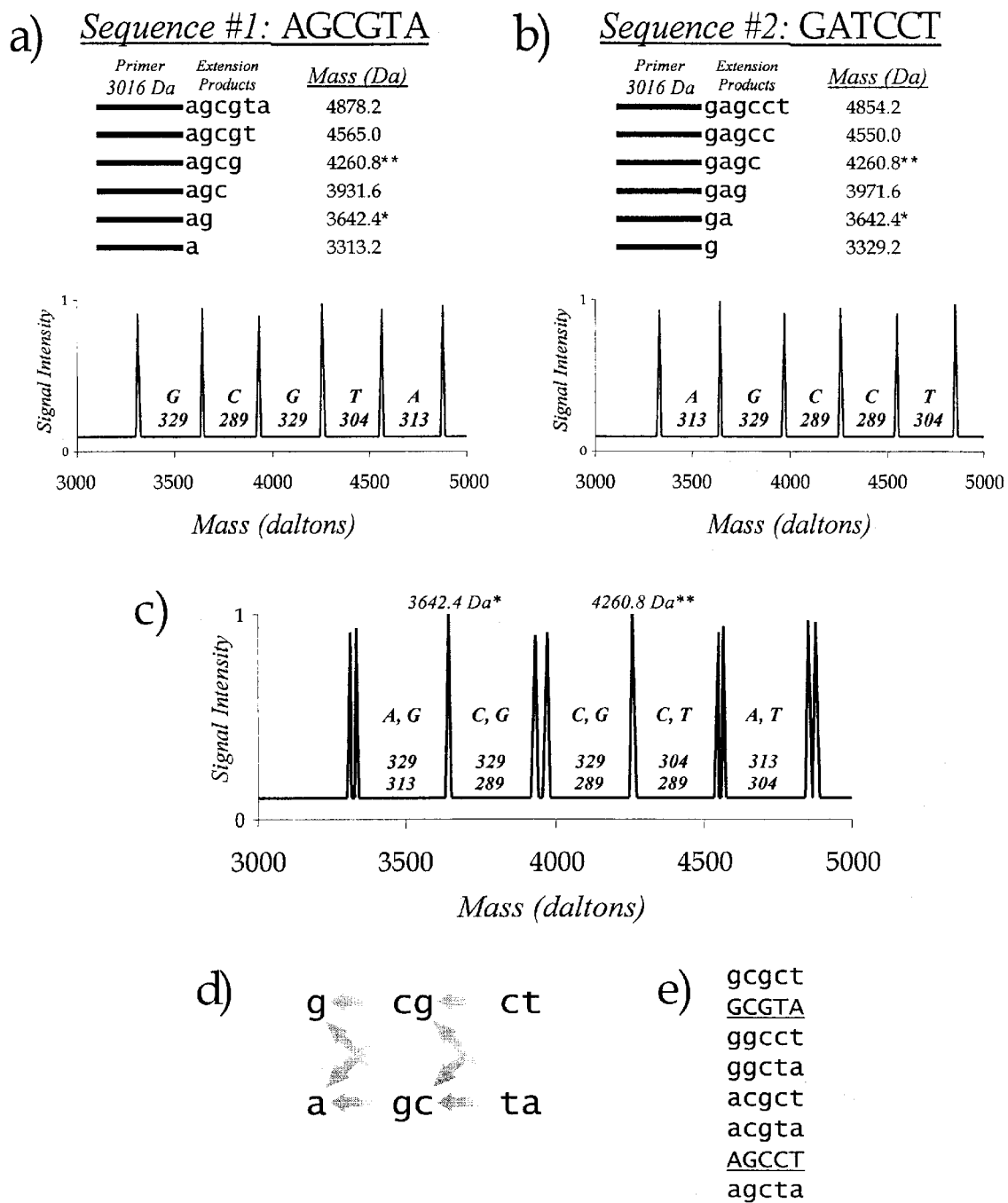
FIG. 1a–b shows that when a single spectrum is used to analyze the products of a conventional Sanger sequencing reaction, where chain termination is achieved at every base position by the incorporation of dideoxynucleotides, the base sequence can be determined by calculation of the mass differences between adjacent peaks (FIGS. 1a and 1b).
Figure 2:
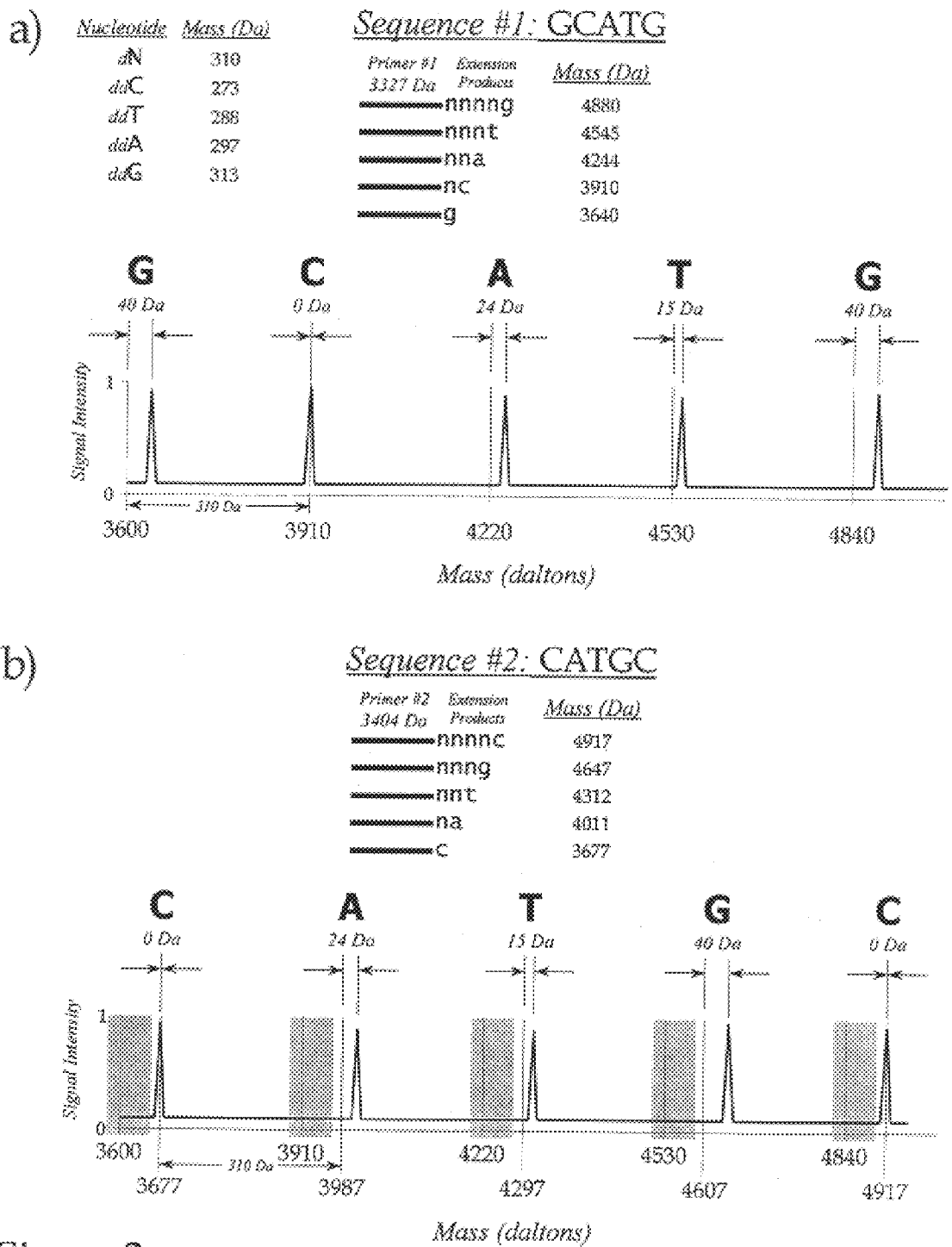
FIG. 2a–b shows implementation of forced mass modulation using mass-matched deoxynucleotides.

Unless defined otherwise, all technical and scientific terms used herein have the same meaning as is commonly understood by one of skill in the art to which this invention belongs. All patents, patent applications, Genbank and other sequence repository sequences, and publications referred to herein are incorporated by reference.

As used herein, a biopolymer includes, but is not limited to, nucleic acid, proteins, polysaccharides, lipids and other macromolecules. Nucleic acids include DNA, RNA, and fragments thereof. Nucleic acids may be derived from genomic DNA, RNA, mitochondrial nucleic acid, chloroplast nucleic acid and other organelles with separate genetic material.

As used herein "nucleic acid" refers to polynucleotides such as deoxyribonucleic acid (DNA) and ribonucleic acid (RNA). The term should also be understood to include, as equivalents, derivatives, variants and analogs of either RNA or DNA made from nucleotide analogs, single (sense or antisense) and double-stranded polynucleotides. Deoxyribonucleotides include deoxyadenosine, deoxycytidine, deoxyguanosine and deoxythymidine. For RNA, the uracil base is uridine.

As used herein, "forced mass modulation" refers to methods provided herein that use deoxynucleotide analogs, modified nucleotide terminators, mass-labeled primers, mass-staggered primers and other such nucleotides, nucleic acids and analogs thereof, to unambiguously assign peak positions of mass fragments of oligonucleotides according to their base position, base identity, and target sequence from which the fragments arose. The method is used to sequence, detect or identify single oligonucleotide or plurality thereof. Hence the method is used, for example for muliplex sequencing and detection of nucleic acid molecules among mixtures thereof.

As used herein, "nucleotides" include, but are not limited to, the naturally occurring nucleoside mono-, di-, and triphosphates: deoxyadenosine mono-, di- and triphosphate; deoxyguanosine mono-, di- and triphosphate; deoxythymidine mono-, di- and triphosphate; and deoxycytidine mono-, di- and triphosphate (referred to herein as dA, dG, dT and dC or A, G, T and C, respectively). Nucleotides also include, but are not limited to, modified nucleotides and nucleotide analogs such as deazapurine nucleotides, e.g., 7-deaza-deoxyguanosine (7-deaza-dG) and 7-deaza-deoxyadenosine (7-deaza-dA) mono-, di- and triphosphates, deuterodeoxythymidine (deutero-dT) mon-, di- and triphosphates, methylated nucleotides e.g., 5-methyideoxycytidine triphosphate, $^{13}C/^{15}N$ labelled nucleotides and deoxyinosine mono-, di- and triphosphate. For those skilled in the art, it will be clear that modified nucleotides and nucleotide analogs can be obtained using a variety of combinations of functionality and attachment positions.

As used herein, a complete set of chain-elongating nucleotides refers to the four different nucleotides or analogs thereof that hybridize to each of the four different bases comprising the nucleic acid template.

As used herein, the term "mass-matched nucleotides" refers to a set of nucleotide analogs wherein each analog is of identical mass to each of the other analogs. For example, analogs of dA, dG, dC and dT can form a mass-matched nucleotide set, when each analog is selected to have the same molecular weight as the others in the set. Mass-matched nucleotide sets can be identified by selecting chemically modified derivatives of natural bases or by the use of a universal base analog such as deoxyinosine or 5-nitroindole and 3-nitropyrrole (5-nitroindole and 3-intropyrrole can be in the dideoxy form) which can form base pairs with more than one of the natural bases. Others include, 3-methyl 7-propynyl isocarbostyril, 5-methyl isocarbostyril, and 3-methyl isocarbostyril. As a result, oligonucleotides that contain such bases differ in molecular weight only as a function of length thereof. Furthermore, incorporation of a single nucleotide(s) that is (are) not in the set renders such the oligonucleotide(s) readily identifiable by mass, particularly by spectrometric analysis.

As used herein, the term "pair-matched nucleotides" refers to a nucleotide set in which the nucleotide analogs are selected such that the total mass each base pair is identical. For example, replacing dG with the nucleotide analog 7-deaza-dG forces the mass of each base pair, i.e., (dA+dT) and (dC+7-deaza-dG) to be identical. Exemplary pair-matched nucleotides, include, but are not limited to, 7-deaza-dA+phosphorothioate-dT ((312.2+320.2)=632.4 Da) and 5-methyl-dC+dG ((303.2+329.2)=632.4 Da); phosphorothioate-7-deaza-dA+dU ((328.2+290.2)=618.4 Da) and dC+dG=((289.2+329.2)=618.4 Da), and other such pairs that may be readily selected. Another exemplary set of mass-matched nucleotides with a molecular mass of 328.2: 7-deaza-dG, phosphorothioate-7-deaza-dA, 5-propynyl-dU and 5-cyano-methyl-2'-deoxycytidine.

As used herein, the term "nucleotide terminator" or "chain terminating nucleotide" refers to a nucleotide analog that terminates nucleic acid polymer (chain) extension during procedures wherein a DNA template is being sequenced or replicated. The standard chain terminating nucleotides, i.e., nucleotideterminators include 2',3'-dideoxynucleotides (ddATP, ddGTP, ddCTP and ddTTP, also referred to herein as dideoxynucleotide terminators). As used herein, dideoxynucleotide terminators also include analogs of the standard dideoxynucleotide terminators, e.g., 5-bromo-dideoxyuridine, 5-methyl-dideoxycytidine and dideoxyinosine are analogs of ddTTP, ddCTP and ddGTP, respectively.

As used herein, "mass-matched terminators" refers to a set of nucleotide terminators that are selected such that each analog of ddA, ddG, ddC and ddT making up the mass-matched set has exactly the same molecular weight. Mass-matched terminator sets can be constructed by selecting chemically modified derivatives of standard dideoxynucleotides or by the use of a universal dideoxynucleotide analog that form base pairs with more than one of the natural bases. Exemplary mass-matched nucleotides include, but are not limited to, 3-methyl 7-propynyl isocarbostyril, 5-methyl iscarbostyril and 3-methyl iscarbostyril. As used herein, the terms "oligonucleotide" or "nucleic acid" refer to single-stranded and/or double-stranded polynucleotides such as deoxyribonucleic acid (DNA), and ribonucleic acid (RNA) as well as derivatives of either RNA or DNA into which nucleotide or dideoxynucleotide analogs have been incorporated. Also included in the term "nucleic acid" are analogs of nucleic acids such as peptide nucleic acid (PNA), phosphorothioate DNA, and other such analogs and derivatives.

As used herein, "nucleotide composition" or "base composition" refers to the numerical ratio of the four nucleotide bases relative to each other in an oligonucleotide.

As used herein, a target nucleic acid refers to any nucleic acid of interest in a sample. It can contain one or more nucleotides. A target nucleotide sequence refers to a particular sequence of nucleotides in a target nucleic acid molecule. Detection or identification of such sequence results in detection of the target and can indicate the presence or absence of a particular mutation or polymorphism.

As used herein, "partially duplex hairpin" refers to a partially self-complementary oligonucleotide, which forms intramolecular base-pairs within its self-complementary region, leaving a "loop" of bases at one end of the molecule and a single-stranded "overhang" region at the other end. Thus, the oligonucleotide assumes a hairpin-like motif. "Blunt-ended hairpin structures", as referred to herein, are similar to the partially duplex hairpin structures with the exception that they do not have a single-stranded "overhang" region.

As used herein, "base periodicity" or "period" ($P_{base}$) refers to the quasi-periodic distribution of the molecular weights of products obtained using Forced Mass Modulation. The base periodicity results from either the mass of the mass-matched deoxynucleotide set, or the mass of the pair-matched deoxynucleotide set, or from the modified chain terminators depending on the embodiment implemented. The base sequence or nucleic acid molecule identity is encoded in the pattern (or detectable therein) in which the observed mass distribution deviates from absolute regular periodicity.

As used herein, the "periodic reference mass" at base position "n" in any given oligonucleotide molecule, $M_{PR}[n]$, is defined as the sum of: (i) the mass of the primer ($M_{primer}$) used to sequence the DNA template using Forced Mass Modulation, (ii) the mass of the lightest nucleotide terminator ($M_{light}$), and, (iii) (n-1) multiple of the base periodicity $P_{base}$.

As used herein, the "positional mass difference" or "mass shift" at base position "n" in any given oligonucleotide molecule, $M_{diff}[n]$, is defined as the distance in daltons between the observed peak, $M_{obs}[n]$, and the nth periodic reference mass.

As used herein, the "maximum mass shift" $S_{max}$ is the maximum possible value of the positional mass difference, depending on the choice of mass-matched nucleotides and nucleotide terminators used in the implementation of Forced Mass Modulation. Accordingly, the maximum mass shift can be modulated by the choice of mass-matched nucleotides and nucleotide terminators.

As used herein, a "primer" refers to an oligonucleotide that is suitable for hybridizing, chain extension, amplification and sequencing. Similarly, a probe is a primer used for hybridization. The primer refers to a nucleic acid that is of low enough mass, typically about between about 5 and 200 nucleotides, generally about 70 nucleotides or less than 70, and of sufficient size to be conveniently used in the methods of amplification and methods of detection and sequencing provided herein. These primers include, but are not limited to, primers for detection and sequencing of nucleic acids, which require a sufficient number nucleotides to form a stable duplex, typically about 6–30 nucleotides, about 10–25 nucleotides and/or about 12–20 nucleotides. Thus, for purposes herein, a primer is a sequence of nucleotides of any suitable length, typically containing about 6–70 nucleotides, 12–70 nucleotides or greater than about 14 to an upper limit of about 70 nucleotides, depending upon sequence and application of the primer.

As used herein, the term "mass-labeled primers" refers to a set of primers that differ in mass by values that provide distinct and resolvable positional mass differences for each of the four termination reactions in an embodiment of Forced Mass Modulation. In this particular embodiment of Forced Mass Modulation, each of the termination reactions for a given oligonucleotide is carried out separately using each of the mass-labeled primers, and the reaction products are combined prior to obtaining a mass spectrum.

As used herein, the term "mass-staggered primers" refers to the mass difference ("staggering" of the masses) between the primers used in multiplexed sequencing using Forced Mass Modulation. For resolution of multiple sequences using this method, the differences between the masses of the primers should at least be equal to the maximum mass shift, and is generally greater than the maximum mass shift by at least 20 daltons to account for the finite width of each observed peak.

As used herein, reference to mass spectrometry encompasses any suitable mass spectrometric format known to those of skill in the art. Such formats include, but are not limited to, Matrix-Assisted Laser Desorption/Ionization, Time-of-Flight (MALDI-TOF), Electrospray (ES), IR-MALDI (see, e.g., published International PCT application No.99/57318 and U.S. Pat. No. 5,118,937), Ion Cyclotron Resonance (ICR), Fourier Transform and combinations thereof. MALDI, particular UV and IR, are among the preferred formats.

As used herein, mass spectrum refers to the presentation of data obtained from analyzing a biopolymer or fragment thereof by mass spectrometry either graphically or encoded numerically.

As used herein, pattern with reference to a mass spectrum or mass spectrometric analyses, refers to a characteristic distribution and number of signals (such peaks or digital representations thereof).

As used herein, signal in the context of a mass spectrum and analysis thereof refers to the output data, which the number or relative number of molecules having a particular mass. Signals include "peaks" and digital representations thereof.

As used herein, "mass spectrum division multiplexing" is an embodiment of Forced Mass Modulation in which unambiguous resolution of multiple sequences in a single spectrum is possible by judicious selection of mass staggered primers.

As used herein, "analysis" refers to the determination of certain properties of a single oligonucleotide, or of mixtures of oligonucleotides. These properties include, but are not limited to, the nucleotide composition and complete sequence of an oligonucleotide or of mixtures of oligonucleotides, the existence of single nucleotide polymorphisms between more than one oligonucleotide, the masses and the lengths of oligonucleotides and the presence of a molecule or sequence within molecule in a sample.

As used herein, "multiplexing" refers to the simultaneous determination of more than one oligonucleotide molecule, or the simultaneous analysis of more than one oligonucleotide, in a single mass spectrometric or other sequence measurement, i.e., a single mass spectrum or other method of reading sequence.

As used herein, "polymorphisms" refer to variants of a gene or an oligonucleotide molecule that differ at more than one base position. In "single nucleotide polymorphisms", the variants differ at only a single base position.

As used herein, amplifying refers to means for increasing the amount of a bipolymer, especially nucleic acids. Based on the 5' and 3' primers that are chosen, amplification also serves to restrict and define the region of the genome which is subject to analysis. Amplification can be by any means known to those skilled in the art, including use of the polymerase chain reaction (PCR) etc. Amplification, e.g., PCR must be done quantitatively when the frequency of polymorphism is required to be determined.

As used herein, "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides in length. Thus, a polymorphism, e.g. genetic variation, refers to a variation in the sequence of a gene in the genome amongst a population, such as allelic variations and other variations that arise or are observed. Thus, a polymorphism refers to the occurrence of two or more genetically determined alternative sequences or alleles in a population. These differences can occur in coding and non-coding portions of the genome, and can be manifested or detected as differences in nucleic acid sequences, gene expression, including, for example transcription, processing, translation, transport, protein processing, trafficking, DNA synthesis, expressed proteins, other gene products or products of biochemical pathways or in post-translational modifications and any other differences manifested amongst members of a population. A single nucleotide polymorphism (SNP) refers to a polymorphism that arises as the result of a single base change, such as an insertion, deletion or change in a base.

A polymorphic marker or site is the locus at which divergence occurs. Such site may be as small as one base pair (an SNP). Polymorphic markers include, but are not limited to, restriction fragment length polymorphisms, variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu. Polymorphic forms also are manifested as different mendelian alleles for a gene. Polymorphisms may be observed by differences in proteins, protein modifications, RNA expression modification, DNA and RNA methylation, regulatory factors that alter gene expression and DNA replication, and any other manifestation of alterations in genomic nucleic acid or organelle nucleic acids.

As used herein, "polymorphic gene" refers to a gene having at least one polymorphic region.

As used herein, "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

As used herein, "predominant allele" refers to an allele that is represented in the greatest frequency for a given population. The allele or alleles that are present in lesser frequency are referred to as allelic variants.

As used herein, a subject, includes, but is not limited to, animals, plants, bacteria, viruses, parasites and any other organism or entity that has nucleic acid. Among subjects are mammals, preferably, although not necessarily, humans. A patient refers to a subject afflicted with a disease or disorder.

As used herein, a phenotype refers to a set of parameters that includes any distinguishable trait of an organism. A phenotype can be physical traits and can be, in instances in which the subject is an animal, a mental trait, such as emotional traits.

As used herein, "resolving power" of a mass spectrometer is the ion separation power of the instrument, i.e., it is a measure of the ability of the mass spectrometer to separate peaks representing different masses. The resolving power R is defined as m/Δm, where m is the ion mass and Δm is the difference in mass between two resolvable peaks in a mass spectrum.

As used herein, "assignment" refers to a determination that the position of a nucleic acid fragment indicates a particular molecular weight and a particular terminal nucleotide.

As used herein, "a" refers to one or more.

As used herein, "plurality" refers to two or more, up to an amount that is governed by the base periodicity, the maximum mass shift, and the resolving power of the mass spectrometer.

As used herein, an array refers to a pattern produced by three or more items, such as three or more loci on a solid support.

As used herein, "distinct" refers to a unique value of molecular weight, mass shift or period that is different from every other value of molecular weight, mass shift or period in the measurement.

As used herein, "unambiguous" refers to the unique assignment of a particular oligonucleotide fragment according to the identity of its terminal base position and, in the event that a number of molecules are multiplexed, that the peak representing an oligonucleotide fragment can also be uniquely assigned to a particular molecule.

As used herein, the symbols $M_C$, $M_T$, $M_A$ and $M_G$ are average molecular weights in daltons of the nucleotides deoxycytidine, thymidine, deoxyadenosine and deoxyguanosine, respectively, or of analogs thereof. $M_{avg}$, the average molecular weight of any given oligonucleotide is a function of the average molecular weights of each of the nucleotides comprising the oligonucleotide, the numbers c, t, a and g of each nucleotide present in the oligonucleotide, the length of the oligonucleotide n' that is the sum of c, t, a and g, and the constant k that represents the mass of any other chemical groups on the molecule, such as terminal phosphates.

As used herein, $N_{TOTAL}$ is the total number of possible base compositions for an oligonucleotide of length n'.

As used herein, "peak separation" or "minimum peak separation" S refers to the minimum value of the distance between consecutive peaks in a mass spectrum that resolves a large number of oligonucleotides having the same lengths but different molecular weights, i.e., different base compositions. The peak separation, which can be tailored by careful selection of the nucleotide analogs incorporated into the oligonucleotide and by a mass spectrometer of desired resolving power, is usually a positive integer greater than one, and typically a positive integer greater than or equal to 3. For two oligonucleotides having the same length n' but different base compositions, their molecular weights will either correspond to the same peak if the molecular weights are identical, or to two peaks separated at least by a value equal to the peak separation.

As used herein, L is the maximum number of allowed oligonucleotide masses for a given nucleotide set. It is directly proportional to the oligonucleotide length n' and the mass difference between the heaviest and lightest nucleotides in the set, and is inversely proportional to the peak separation.

As used herein, D refers to the average density of different base compositions per allowed mass value, given the set of all possible base compositions of an oligonucleotide of length n'.

As used herein, $M_{heavy}$ refers to the mass of the heaviest nucleotide, nucleotide terminator or terminating base pair in daltons, depending on the specific embodiment of Forced Mass Modulation being described.

As used herein, $M_{light}$ refers to the mass of the lightest nucleotide, nucleotide terminator or terminating base pair in daltons, depending on the specific embodiment of Forced Mass Modulation being described.

As used herein, $M_{primer}$ is the mass of the primer in daltons.

As used herein, $M_{obs}[n]$ is the observed mass of the sequencing reaction at the nth base position.

As used herein, $M_{term}[n]$ refers to the mass in daltons of the nth terminating nucleotide.

As used herein, L' is the theoretical upper limit on the number of sequences that be multiplexed in a single mass spectrum. L' is directly proportional to the base periodicity $P_{base}$, and is inversely proportional to the maximum mass shift $S_{max}$.

As used herein, $M_{duplex}$ is the mass in daltons of the fully duplex hairpin primer in the implementation of Forced Mass Modulation using pair-matched nucleotides.

As used herein, $M_{ddM}$ is the mass in daltons of a dideoxy terminator that belongs to a set of mass-matched terminators.

As used herein, $M_{targ}[n]$ is the mass of the nth nucleotide past the priming site in the 3' to 5' direction in the target sequence, i.e., the oligonucleotide whose sequence is being determined.

As used herein, "specifically hybridizes" refers to hybridization of a probe or primer only to a target sequence preferentially to a non-target sequence. Those of skill in the art are familiar with parameters that affect hybridization; such as temperature, probe or primer length and composition, buffer composition and salt concentration and can readily adjust these parameters to achieve specific hybridization of a nucleic acid to a target sequence.

As used herein, a biological sample refers to a sample of material obtained from or derived from biological material, such as, but are not limited to, body fluids, such blood, urine, cerebral spinal fluid and synovial fluid, tissues and organs. Derived from means that sample can be processed, such as by purification or isolation and/or amplification of nucleic acid molecules.

As used herein, a composition refers to any mixture. It may be a solution, a suspension, liquid, powder, a paste, aqueous, non-aqueous or any combination thereof.

As used herein, a combination refers to any association between two or among more items.

As used herein, "kit" refers to a package that contains a combination and optionally instructions and/or reagents and apparatus for use with the combination.

Forced Mass Modulation for Analysis of Nucleic Acid Molecules

Time of Flight Analysis and Drawbacks Thereof

While time-of-flight mass spectrometry offers a number of advantages over conventional techniques such as gel electrophoresis, the peculiar relationship between the masses of the bases in DNA complicates the analysis of complex mixtures of oligonucleotides by mass spectrometry. For a given oligonucleotide, the average molecular weight, $M_{avg}$, is given by the following equation:

$$M_{avg}=k+cM_C+tM_T+aM_A+gM_G \qquad (i)$$

where $M_C$, $M_T$, $M_A$, $M_G$ are the average molecular weights of each of the four nucleotide bases (cytosine, thymine, adenine, guanine) and c, t, a, g represent the number of each base present in the oligonucleotide. The term k is a constant representing the mass of any other chemical groups on the molecule, such as terminal phosphates. Rearranging equation (i) to give the average molecular weight as a function of the length of the oligonucleotide in bases yields $$M_{avg}=k+n'M_C+t(M_T-M_C)+a(M_A-M_C)+g(M_G-M_C) \qquad (ii)$$

where n', the oligonucleotide length, is defined as $$n'=c+t+a+g$$

Substituting the masses of the naturally occurring bases in DNA (to one-tenth dalton):

$M_C$=289.2
$M_T$=304.2
$M_A$=313.2
$M_G$=329.2 into equation (ii) yields $$M_{avg}=k+289.2n'+t(304.2-289.2)+a(313.2-289.2)\\+g(329.2-289.2), \qquad (iii)$$

which can be simplified to $$M_{avg}=k+289.2n'+15t+24a+40g \qquad (iv)$$

Close inspection of equation (iv) reveals that it is almost always possible to find two oligonucleotides of the same length but of different base composition whose average masses differ by only one dalton. For example, all 7-mers having a base composition of $A_2C_2G_2T$ have an average molecular weight of (2167.4+k), while all 7-mers with the base composition $A_3CGT_2$ have an average molecular weight of (2166.4+k). Since the following relation $$(M_C+M_G)=(M_T+M_A)+1$$

is always true for the naturally occurring bases in DNA, simply replacing one C and one G in an oligonucleotide with one A and one T will produce a new oligonucleotide exactly one dalton lighter. Many other "single-dalton difference" relations, such as $$4M_A=(M_C+M_T+2M_G)+1$$

can readily be found for the naturally occurring bases.

Thus, the possibility always exists that two or more oligonucleotides of same length and different molecular weight (and, therefore, different base composition) will be too close in mass to be resolved by a time-of-flight instrument. Two oligonucleotides of same length but different molecular weight differ in base composition unless they are each composed of different nucleotide analogs, whereas two oligonucleotides of same length and same molecular weight can have either the same or different base compositions. This problem becomes increasingly severe with increasing oligonucleotide size, since the total number of possible base compositions, $N_{TOTAL}$, scales as a cubic function of the oligonucleotide length n', in bases:

$$N_{TOTAL} = \frac{(n'+1)(n'+2)(n'+3)}{6} \qquad (v)$$

The use of time-of-flight mass spectrometry in sequencing applications also poses several potential problems. The great drawback of sequencing by the Sanger method is that the molecular weights of the Sanger reaction products can appear virtually anywhere on the mass axis depending on the particular sequence being examined. As a result, the absolute mass of any single Sanger fragment has to be measured with sufficient accuracy to calculate its distance from the masses from the fragments above and below it. Thus, determination of the identity of a single base depends on the accuracy of two separate mass measurements. Any error in a determination mass of a single fragment affects the accuracy of two bases in the sequence.

For longer sequences (30–50 bases), it may not be possible to determine the mass difference between adjacent peaks with sufficient accuracy to unambiguously determine base identity. This is particularly a problem for the nucleotides A and T, which differ in mass only by nine daltons. The problem is addressed by resolving each of the four termination reactions in a separate mass spectrum. In this case each peak functions essentially as binary signal indicating the presence of a base at a particular position, much as in conventional electrophoretic sequencing. Using separate spectra, however, increases read accuracy but at the expense of increasing the number of required mass measurements by a factor of four.

It is possible to resolve two target sequences by the Sanger method in a single mass spectrum, provided that all products of the sequencing reactions have unique and resolvable masses, and multiplex methods using mass modified bases have been developed. But, where two or more reaction products have the same mass, then unambiguous reconstruction of the two target sequences is not possible (see, e.g., FIGS. 1c–e). In addition, there is no way to determine a priori which observed masses belong to a particular sequence. In practice, this means that multiplexed Sanger sequencing by mass spectrometry can be difficult. The methods provided herein resolve these problem and provide a way to determine a priori which masses are associated with extension of a particular primer.

Forced Mass Modulation

As noted above, Forced Mass Modulation refers to methods provided herein that permit unambiguous assignment of peak positions (or masses) to mass fragments of oligonucleotides according to their base position, base identity, and target sequence from which the fragments arose. The methods use deoxynucleotide analogs, modified nucleotide terminators, mass-labeled primers, mass-staggered primers and other such nucleotides, nucleic acids and analogs thereof to provide a means for deconvoluting complex mass spectra or output from other mass determining techniques. These methods permit deconvolution of highly multiplexed nucleic acid reaction mixtures for sequencing methods and detection methods that include a step of primer extension. In practicing these methods, primers are extended using mass-matched nucleotides and chain terminators (or in some embodiments mass where it is only necessary to detect incorporation (or the absence of incorporated) mass-matched terminators and optionally mass-matched chain extending nucleotides). Because the sequence and/or molecular mass of a primer is known, and the extended nucleotides have the same molecular mass, a periodicity in molecular mass that is a function of molecular weight of the selected mass matched nucleotide(s) results.

As described in more detail below, for sequencing reactions using chain terminators, the deviation from the periodicity results from incorporation of a chain terminator. The deviation is a function of the particular terminator incorporated. For detection methods, incorporation of a terminator will indicate the presence of a mutation (if the terminator is selected to pair with the first mutated nucleotide. Any shift from periodicity will indicate the presence of the mutation. These methods, thus provide a simple, reliable way to detect the presence of a mutations or target nucleotide(s) in a sequence and to sequence nucleic acids. Forced mass modulation can be used with any method, such as mass spectrometry and gel electrophoresis, that relies on molecular weight as an output. Mass spectrometry is exemplified herein.

The methods, designated Forced Mass Modulation methods, provided herein, are implemented by suitable selection of nucleotides and/or chain terminators, such as by the use of deoxynucleotide analogs, modified nucleotide terminators and mass-labeled primers in one or more reactions. Forced Mass Modulation can be used to simultaneously sequence or detect large numbers, such twenty-five or more) oligonucleotides, with a high degree of resolution and accuracy. It can also be used to simplify the analysis of closely related sequence variants, as is required in the detection and scoring of nucleotide polymorphisms, including single nucleotide polymorphism (SNPs) and for other genotypical analyses. Forced Mass Modulation greatly improves the use of mass spectrometry for nucleic acid analyses. Nearly every application relies on mass measurements that can benefit in increased accuracy and in a reduction of the number of required spectra. Another advantage of Forced Mass Modulation is the number of different ways in which it can be implemented, allowing it to be tailored to particular experimental or instrumental limitations.

For example, compared to the conventional Sanger methods, Forced Mass Modulation, provides increased accuracy, simplified interpretation of mass data, and the ability to use a single mass spectrum for the unambiguous resolution of several distinct nucleic acid molecules. For mass spectrometry applications, the methods provide unambiguous assignment of peak positions of mass fragments of oligonucleotides according to their base position, base identity, and target sequence from which the fragments arose. Thus, the methods herein are advantageously used for multiplexing, in which a plurality of reactions are run in a single reaction (single pot). Forced Mass Modulation, exemplified with reference to sequencing methods, such as PROBE, can also be adapted to detection methods in which a primer is extended.

In Forced Mass Modulation in which a primer is extended with mass-matched nucleotides, for examples, the molecular weights of extended nucleic acid chains, such as sequencing reaction products, are constrained since all extension products from the same primer will have a molecular weight that differs either by the length of the extension and the chain terminator. As a result, the extension products assume a quasi-periodic distribution on the mass axis with a predetermined base periodicity. For sequencing, the base sequence itself is encoded in the pattern in which the observed mass distribution deviates from absolute regular periodicity. Since the base periodicity will always be known a priori, since the primer is known, each peak in the observed mass spectrum can be matched unambiguously to a unique nucleotide position in the target sequence. The initiating primers fix each set of nested fragments or extended products, and the use of mass-matched nucleotides creates the periodicity.

As demonstrated by the Examples below, the method is advantageous for numerous applications including sequencing and a variety of detection methods, including primer oligo base extension (PROBE) (see, e.g., U.S. Pat. No. 6,043,031; allowed U.S. application Ser. No. 09/287,679; and U.S. Pat. No. 6,235,478) that use mass spectrometry to distinguish between extended primers. If the base compositions of the target oligonucleotides are known a priori then it is possible to select a nucleotide set that produces oligonucleotide masses that are distinct and resolvable for any particular instrument or application.

Conversely, it is also possible to select a nucleotide set that restricts specific oligonucleotides to have the same mass, regardless of a change in base composition. The strategy of restricting specific oligonucleotides to have the same mass can be used to separate more than one oligonucleotide population of different lengths by restricting all oligonucleotides of a particular length to the same molecular weight, irrespective of differences in base composition.

The oligonucleotide analysis or sequencing in methods provided herein can be accomplished by one of several methods employed in the art for the synthesis, resolution and/or detection of nucleic acids. Depending on the embodiment implemented, modified nucleotides can be incorporated into the oligonucleotides by chemical (*Oligonucleotides and Analogues: A Practical Approach*, F. Eckstein, ed., IRL Press Oxford, 1991) or enzymatic (F. Sanger et al., *Proc. Natl. Acad. Sci. USA* 74:5463-67, 1977) synthesis. Extension products or truncated products of the oligonucleotides to be sequenced can be obtained using chemical (A. M. Maxam and W. Gilbert, *Proc. Natl. Acad. Sci. USA* 74:560-64,1977) or enzymatic (F. Sanger et al., *Proc. Natl. Acad. Sci. USA* 74:5463-67, 1977) methods.

For the resolution and detection of target nucleic acids any mass determination method, such as, but are not limited to, chromatography, gel electrophoresis, capillary zone electrophoresis and mass spectrometry, is used. Mass spectrometric formats, include, but are not limited to, are matrix assisted laser desorption ionization (MALDI), electrospray (ES), ion cyclotron resonance (ICR) and Fourier Transform. For ES, the samples, dissolved in water or in a volatile buffer, are injected either continuously or discontinuously into an atmospheric pressure ionization interface (API) and then mass analyzed by a quadrupole. The generation of multiple ion peaks which can be obtained using ES mass spectrometry can increase the accuracy of the mass determination. Even more detailed information on the specific structure can be obtained using an MS/MS quadrupole configuration.

In MALDI mass spectrometry, various mass analyzers can be used, e.g., magnetic sector/magnetic deflection instruments in single or triple quadrupole mode (MS/MS), Fourier transform and time-of-flight (TOF) configurations as is known in the art of mass spectrometry. For the desorption/ionization process, numerous matrix/laser combinations can be used. Ion-trap and reflectron configurations can also be employed.

Pair-matched Nucleotide-based Methods

Forced Mass Modulation can be implemented using a deoxynucleotide set in which the mass of each base pair is identical, termed a pair-matched nucleotide set. A pair-matched nucleotide set can easily be formed, for example, by replacing dG (329.2 Da) in the set of naturally occurring nucleotides with 7-deaza-dG (328.2 Da). This forces the mass of each base pair to be 617.4 daltons:

(dA+dT)=(313.2+304.2)=617.4 Da (dC+7-deaza-dG)=(289.2+328.2)=617.4 Da

Many other pair-matched sets are possible using available nucleotide analogs. For this embodiment, the target DNA sequence can be composed entirely of the pair-matched nucleotide set. This can be accomplished by amplifying the target DNA sequence by PCR using the pair-matched nucleotide set prior to the sequencing reaction.

A further requirement for this embodiment of Forced Mass Modulation is that the mass of each terminating base pair is unique and resolvable. The standard dideoxy terminators therefore cannot be used with the pair-matched nucleotide set described above, because the masses of all terminating base pairs are identical at 601.4 daltons, except ddG:dC, which is 602.4 daltons. For the sake of clarity in this example, it is assumed that a set of mass-matched terminators is available ("ddM," defined as set of chain-terminating nucleotides that have exactly the same molecular weight ddA=ddC=ddG=ddT). If the mass of ddM is arbitrarily chosen to be 500 daltons, then the masses of the terminating base pairs are as follows:

| Terminating Base Pair | Mass (Da) |
|---|---|
| ddM: dC | 789.2 |
| ddM: dT | 804.2 |
| ddM: dA | 813.2 |
| ddM: 7-deaza-dG | 828.2 |

In practice it is also possible to implement Forced Mass Modulation using a set of terminators that have different masses, this is discussed in detail below.

Exemplary embodiments in which the mass shift is obtained using pair-matched nucleotides, where the mass of each nucleotide base-pair is selected so that the masses of all pairs are identical, are described in Example 4. In one embodiment thereof, the following steps are performed: (i) the target nucleic acid is copied or amplified by a method such as PCR in the presence of the pair-matched nucleotide set prior to the sequencing or detection reaction; (ii) the target nucleic acid is denatured, and a partially duplex hairpin primer is annealed and ligated to the single-stranded template; (iii) the primer is extended in the presence of chain terminating nucleotides and pair-matched nucleotides to produce extension products; (iv) the masses of the extension products follow a periodic distribution that is determined by the mass of the pair-matched nucleotide set, and, (v) the target nucleic acid is detected by virtue of its molecular weight or its sequence is determined from the mass shift of each extension product from its corresponding periodic reference mass.

In embodiments described above, the extending bases are pair matched. the mass of each terminating base pair is unique and resolvable, so that the mass shifts corresponding to each terminating base pair are unique. The nucleotide terminators are optionally mass-matched or can be of distinct masses as long as distinct values of mass shift are obtained for each terminating base pair.

In another embodiment, the extension products are treated to produce blunt-ended double-stranded extension products by methods known to those of skill in the art, such as the use of single-strand specific nucleases. In an aspect of this embodiment, a plurality of target nucleic acids can be multiplexed in a single reaction by annealing each target nucleic acid to a primer of distinct molecular weight. The primers can be selected to differ in molecular weight by a value that is greater than the maximum mass shift, i.e., the difference in molecular weight between the heaviest and the lightest nucleotide terminating base pairs. Since double stranded nucleic acid can be analyzed, the effective sequence read is halved relative to the embodiment employing mass-matched nucleotides, but the number of molecules that can be multiplexed is doubled, due to the increase in period (the value of the mass of a base pair, rather than a single mass-matched nucleotide). In exemplary embodiments, about 14 to about 50 sequences are multiplexed. In detection embodiments, about 50 or more molecules can be simultaneously multiplexed since only a single terminating base pair is added in the extension reaction.

In another embodiment, the chain termination reactions can each be carried out separately using a standard nucleotide terminator, pair-matched nucleotides, and mass-labeled primers, if modified nucleotide terminators which are either mass-matched or provide distinct values of mass shift for each terminating base pair are not available. The reactions can be pooled prior to detection or sequence analysis. In one embodiment, the mass-labeled primers can have distinct values of molecular weight that give rise to unique values of mass shift or positional mass difference for each terminating base.

Optimizing the Mass Spectrometric Analysis of Oligonucleotide Mixtures

In another method provided herein, nucleotide analogs are used to restrict the possible values of molecular weights that an oligonucleotide can possess relative to other oligonucleotides of the same length. The nucleotide analogs can be incorporated into the oligonucleotides using any suitable method, such as automated DNA synthesis (*Oligonucleotides and Analogues: A Practical Approach*, F. Eckstein, ed., IRL Press Oxford, 1991) or by enzymatic replication using a polymerase and the requisite nucleotides and nucleotide analogs.

For example, any two oligonucleotides with the same length n' with different base compositions can either 1) have exactly the same average molecular weight, or 2) have molecular weights no closer than a minimum value called the peak separation. In most cases, the peak separation will be a positive integer greater than one, but fractional values are theoretically possible.

To illustrate an exemplary implementation of this method, the average molecular weight of the nucleotide analog 7-deaza-dG (328.2 daltons) can be substituted for $M_G$, into equation (ii) above, which defines $M_{avg}$ as a function of the length "n" of the oligonucleotides in bases, as follows:

(ii) $M_{avg}=k+n'M_C+t(M_T-M_C)+a(M_A-M_C)+g(M_G-M_C)$, where $M_C$, $M_T$, $M_A$, $M_G$ are the average molecular weights of each of the four nucleotide bases (cytosine, thymine, adenine, guanine); c, t, a, g represent the number of each base present in the oligonucleotide, the sum thereof, i.e., c+t+a+g=n', the total oligonucleotide length in bases; and the term k is a constant representing the mass of any other chemical groups on the molecule, such as terminal phosphates. Substituting the masses of the naturally occurring bases dC, dT and dA in DNA (to one-tenth dalton), and of 7-deaza-dG, $M_C=289.2$ $M_T=304.2$ $M_A=313.2$ $M_G=328.2$ and following simplification, the equation reduces to:

$$M_{avg}=k+289.2n'+15t+24a+39g$$

Extracting the common factor from the last three terms yields $$M_{avg}=k+289.2n'+(5t+8a+13g)\times 3 \quad (vi)$$

In this example, the minimum peak separation is three daltons. It is not possible to identify or detect two oligonucleotides of the same length with different molecular weights that are closer than three daltons. Oligonucleotides with average masses closer than three daltons the oligonucleotides are detected if they are of different lengths.

As a second example, $M_T$ can be substituted with the molecular weight of a hypothetical nucleotide analog whose mass is 305.2 into equation (ii), yielding $$M_{avg}=k+289.2n'+16t+24a+40g$$

Extracting the common integer factor from the last three terms yields $$M_{avg}=k+289.2n'+(2t+3a+5g)\times 8 \quad (vii)$$

for a minimum peak separation of eight daltons. Thus, appropriate selection of nucleotide analogs permits construction of nucleotide sets that provides sufficient peak separation for adequate resolution by mass, such as in a time-of-flight mass spectrometer. The trade-off for a greater peak separation is a greater number of base compositions that have exactly the same mass for a given oligonucleotide length. The maximum number of allowed oligonucleotide masses, L, for a given nucleotide set, is given by $$L = \frac{n'(M_{heavy}-M_{light})}{S}+1, \quad (viii)$$

where n' is the oligonucleotide length in bases, S is the peak separation, $M_{light}$ the mass of the lightest nucleotide in the set, $M_{heavy}$ is the mass of the heaviest nucleotide in the set. The number of allowed oligonucleotide masses scales in direct proportion to the base length and inversely with the peak separation, but not all possible mass values will be represented for a given oligonucleotide length, particularly for small n. The average density of different base compositions per allowed mass value, D, can be obtained by dividing equation (v) by (viii)

$$D = \frac{N_{TOTAL}}{L},$$

which expands into $$D = \frac{S(n'+1)(n'+2(n'+3)}{6(n'(M_G-M_C)+S)} \quad (ix)$$

using a typical nucleotide set with G as the heaviest base and C as the lightest. The density function scales in direct proportion to the peak separation and as a quadratic function of the oligonucleotide length in bases. In practice, the average density of base compositions per allowed mass value predicated by equation (ix) will be somewhat lower than the actual density of base compositions per observed mass value, because not all allowed masses will always be represented. The Examples describe implementation of the methods for sequencing.

System and Software Method for Force Mass Modulation

Also provided are systems that automate the methods for determining a nucleotide sequence of a target nucleic acid or the detection methods provided herein using a computer programmed for identifying the sequence or target nucleic acid identity based upon the methods provided herein. The methods herein can be implemented, for example, by use of the following computer systems and using the following calculations, systems and methods.

An exemplary automated testing system contains a nucleic acid workstation that includes an analytical instrument, such as a gel electrophoresis apparatus or a mass spectrometer or other instrument for determining the mass of a nucleic acid molecule in a sample, and a computer capable of communicating with the analytical instrument (see, e.g., copending U.S. application Ser. Nos. 09/285,481, 09/663,968 and 09/836,629; see, also International PCT application No. WO 00/60361 for exemplary automated systems). In an exemplary embodiment the computer is an IBM compatible computer system that communicates with the instrument using a known communication standard such as a parallel or serial interface.

For example, systems for analysis of nucleic acid samples are provided. The systems include a processing stations that performs a forced mass modulation chain extension reaction; a robotic system that transports the resulting products from the processing station to a mass measuring station, where the masses of the products of the reaction are determined; and a data analysis system, such as a computer programmed to identify nucleotides using forced mass modulation data, that processes the data from the mass measuring station to identify a nucleotide or plurality thereof in a sample or plurality thereof. The system can also include a control system that determines when processing at each station is complete and, in response, moves the sample to the next test station, and continuously processes samples one after another until the control system receives a stop instruction.

The computer can be part of the instrument or another system component or it can be at a remote location. A computer system located at a site distant from the instrument can communicate wit the instrument, for example, through a wide area network or local area communication network or other suitable communication network. The system with the computer is programmed to automatically carry out steps of the methods herein and the requisite calculations. For embodiments that use mass-matched deoxyriboucleotides, a user enters the primer sequence or primer mass, the periodic reference mass and mass of an individual mass-matched deoxyonucleotide. These data can be directly entered by the user from a keyboard or from other computers or computer systems linked by network connection, or on removable storage medium such as a CD-ROM, minidisk (MD), DVD, floppy disk or other suitable storage medium. Next the user causes execution software that operates the system in which the mass spectrum of the extension products is generated. The Forced Mass Modulation software performs the steps of obtaining the masses of the fragments generated by the sequencing reaction and measured by the analytical instrument, and determining the identity of a nucleotide at any base position or the positional mass difference. The identity of the nucleotide at each base position is determined by comparing the calculated $M_{diff}[n]$ values to a database of previously calculated values of Mdiff for each of the chain terminating nucleotides.

$$M_{diff}[n]=M_{obs}[n]-M_{PR}[n],$$

where:

$$M_{PR}[n]=(M_{primer}+M_{light})+(n-1)P_{base}, \quad (i)$$

in which n is the base position, $M_{PR}[n]$ is the $n^{th}$ periodic reference mass, $M_{primer}$ is the mass of the primer, $M_{light}$ is the mass of the lightest nucleotide terminator and $P_{base}$ is the base periodicity in daltons. The observed masses of the sequencing reaction products are given by the following equation:

$$M_{obs}[n]=M_{primer}+(n-1)P_{base}+M_{term}[n], \quad (ii)$$

where n is the base position, $M_{obs}[n]$ is the $n^{th}$ observed mass, $P_{base}$ is the base periodicity, and $M_{term}[n]$ is the mass of the $n^{th}$ terminating nucleotide in daltons. The positional mass differences for the sequence can be obtained by subtracting equation (i) from equation (ii) and evaluating at every base position n:
where $M_{diff}[n]$ is the $n^{th}$ positional mass difference. This relation simplifies to:

$$M_{diff}[n]=M_{term}[n]-M_{light}. \quad (iii)$$

Figure 2A:
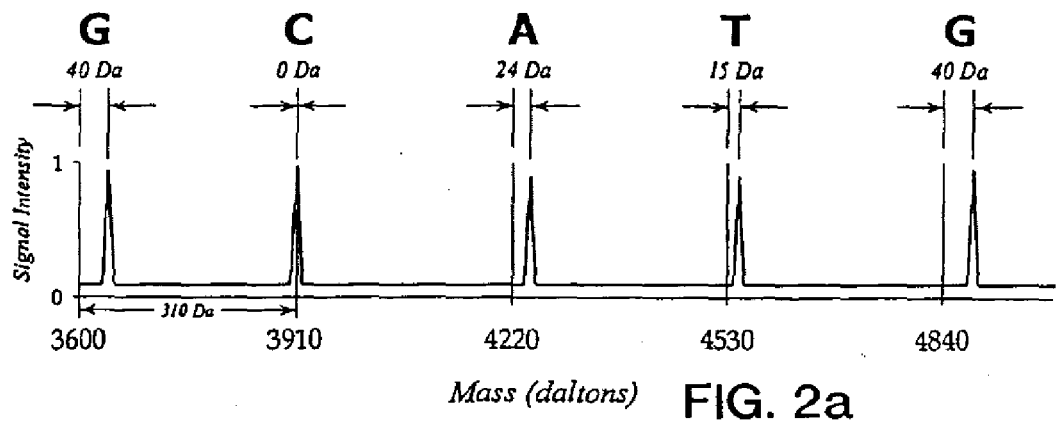

Hence, the periodicity is determined by the mass of the mass-matched nucleotide and the shift is the difference in location of a peak resulting from the chain terminator. For example, in FIG. 2a, the lightest terminator is ddC, and the differential is 0 for C, 40 for G, 34 for A, 15 for T. The selected mass matched nucleotide has a mass of 310 Da. The primer in FIG. 2a has a mass of 3327 Da and the first peak would be at 3600 if the first nucleotide in the extension product were C (0 shift). Since the first peak is at 3640, the shift is 40 Da. Therefore the first nucleotide is G, corresponding to a shift from the periodicity of 310 Da generated by the mass-matched nucleotides.

Detection Methods

The methods herein may be used with any method for detection of nucleic acids based on molecular mass known to those of skill in the art, particularly methods in which a primer is extended. Such methods are modified by extending using mass matched nucleotides and/or chain terminators in extension reactions. Alternatively, or additionally, amplification reactions may be performed using mass-matched nucleotides or pair-matched sets of nucleotides. These methods can be readily multiplexed using the methods and nucleic acid molecules provided herein.

Detection methods and protocols, including those that rely on mass spectrometry (see, e.g., U.S. Pat. Nos. 6,194,144; 6,225,450; 5,691,141; 5,547,835; 6,238,871; 5,605,798; 6,043,031; 6,197,498; 6,235,478; 6,221,601; 6,221,605; International PCT application No. WO 99/31273, International PCT application No. WO 98/20019), can be modified for use with the methods herein by using mass-matched nucleotides for extension or pair matched duplexes for hybridization reactions.

Among the methods of analysis herein are those involving the primer oligo base extension (PROBE) reaction with mass spectrometry for detection. In such reactions, the primer will be extended by mass-matched nucleotides. The methods herein are designed for multiplexing so that a plurality of different primers can be extended at different loci in the same reaction. The PROBE method uses a single detection primer followed by an oligonucleotide extension step to give products, which can be readily resolved by mass spectrometry, and, in particular, MALDI-TOF mass spectrometry. The products differ in length depending on the presence or absence of a polymorphism. In this method, a detection primer anneals adjacent to the site of a variable nucleotide or sequence of nucleotides and the primer is extended using a DNA polymerase in the presence of one or more dideoxy NTPs and, optionally, one or more deoxy NTPs. The resulting products are resolved by MALDI-TOF mass spectrometry. The mass of the products as measured by MALDI-TOF mass spectrometry makes possible the determination of the nucleotide(s) present at the variable site. Use of primers containing mass-matched bases increases the resolving power of the reaction and permit simultaneous detection of a plurality of mutations (polymorphisms).

These methods can be automated (see, e.g., copending U.S. application Ser. No. 09/285,481 and published International PCT application No. PCT/US00/08111, which describes an automated process line) and performed in a system that includes a computer programmed for analysis of the mass data as described above.

The analyses can be performed on chip based formats in which the target nucleic acids or primers are linked to a solid support, such as a silicon or silicon-coated substrate, preferably in the form of an array. Generally, when analyses are performed using mass spectrometry, particularly MALDI, small nanoliter volumes of sample are loaded on, such that the resulting spot is about, or smaller than, the size of the laser spot. It has been found that when this is achieved, the results from the mass spectrometric analysis are quantitative. The area under the signals in the resulting mass spectra are proportional to concentration (when normalized and corrected for background). Methods for preparing and using such chips are described in U.S. Pat. No. 6,024,925, co-pending U.S. application Ser. Nos. 08/786,988, 09/364,774, 09/371,150 and 09/297,575; see, also U.S. application Ser. No. PCT/US97/20195, which published as WO 98/20020. Chips and kits for performing these analyses are commercially available from SEQUENOM under the trademark MassARRAY. MassArray relies on the fidelity of the enzymatic primer extension reactions combined with the miniaturized array and MALDI-TOF (Matrix-Assisted Laser Desorption Ionization-Time of Flight) mass spectrometry to deliver results rapidly. It accurately distinguishes single base changes in the size of DNA fragments associated with genetic variants without tags.

The following Examples are included for illustrative purposes only and are not intended to limit the scope of the invention.

EXAMPLE 1

Forced Mass Modulation using Mass-Matched Deoxynucleotides

For this implementation, a set of nucleotide analogs for the four bases in DNA are selected (Amersham Pharmacia Biotech) such that each base has exactly the same molecular weight, termed a mass-matched deoxynucleotide set. This is achieved by judiciously choosing chemical modifiers of the existing bases or by the using a universal base analog such as deoxyinosine, which can form base pairs with more than one of the natural bases. For this example, the mass of each deoxynucleotide ("dN") in the mass-matched set has the arbitrarily selected value of 310 daltons, but any other value suffices. The sequencing reaction is performed as follows: 1) a primer is annealed to the target to be sequenced; 2) the resulting structure is subjected to an extension reaction using a suitable polymerase in the presence of the mass-matched nucleotide set and the four standard dideoxynucleotide terminators. The products and molecular masses of such a reaction are shown with a simulated mass spectrum in FIG. 2a. The base periodicity is the mass of dN, or 310 daltons. The identity of a nucleotide at any base position is given by the positional mass difference, defined as the distance in daltons between the observed peak and the nearest periodic reference mass, which occurs every 310 daltons. In this example, the first periodic reference mass is defined as the (primer mass+ddC), or (3327+273)=3600 daltons. The second periodic reference mass would be 3600 plus the base periodicity or (3600+310)=3910, and so on. Expressed in terms of the base position n:

$$M_{PR}[n]=(M_{primer}+M_{light})+(n-1)P_{base}, \quad (i)$$

where n is the base position, $M_{PR}[n]$ is the $n^{th}$ periodic reference mass, $M_{primer}$ is the mass of the primer, $M_{light}$ is the mass of the lightest nucleotide terminator and $P_{base}$ is the base periodicity in daltons. The observed masses of the sequencing reaction products are given by the following equation:

$$M_{obs}[n]=M_{primer}+(n-1)P_{base}+M_{term}[n], \quad (ii)$$

where n is the base position, $M_{obs}[n]$ is the $n^{th}$ observed mass, $P_{base}$ is the base periodicity, and $M_{term}[n]$ is the mass of the $n^{th}$ terminating nucleotide in daltons. The positional mass differences for the sequence can be obtained by subtracting equation (i) from equation (ii) and evaluating at every base position n:

$$M_{diff}[n]=M_{obs}[n]-M_{PR}[n],$$

where $M_{diff}[n]$ is the $n^{th}$ positional mass difference. This relation simplifies to:

$$M_{diff}[n]=M_{term}[n]-M_{light}. \quad (iii)$$

Inspection of equation (iii) reveals that $M_{diff}$ can only take on four distinct values, each corresponding to a different nucleotide terminator:

$M_{diff}[\text{``ddC''}]=(273.2-273.2)=0$ $M_{diff}[\text{``ddT''}]=(288.2-273.2)=15$ $M_{diff}[\text{``ddA''}]=(297.2-273.2)=24$ $M_{diff}[\text{``ddG''}]=(313.2-273.2)=40$.

Hence, the identity of the nucleotide at every base position in the target sequence can be determined by comparing each calculated positional mass difference with the values in the table above. Since the values that $M_{diff}$ can assume depend only on the choice of nucleotide terminators used in the sequencing reaction, it is possible to tailor the positional mass differences so that they are resolvable for any particular mass spectrometer. For example, replacing the terminator ddT with its analog 5-bromo-dideoxyuridine (353.1 daltons) yields a positional mass difference of (353.1−273.2)=79.9 Da for termination at T positions in the target sequence. This type of nucleotide substitution can be particularly valuable for lower-resolution mass spectrometers, as it possible to maintain the sequence read accuracy without requiring any additional mass spectra.

Further inspection of equation (iii) reveals that each observed mass value can be at most 40 daltons heavier than the nearest periodic reference mass. This limit is termed the maximum mass shift and is defined as the mass difference between the heaviest nucleotide terminator and the lightest. Resolving a second target sequence by Forced Mass Modulation with the standard dideoxy terminators is possible in a single spectrum so long as the primer for the second sequence is at least 40 daltons heavier (the maximum mass shift) than the primer for the first sequence, thus insuring that the peaks for each sequence never overlap in mass.

Figure 3:
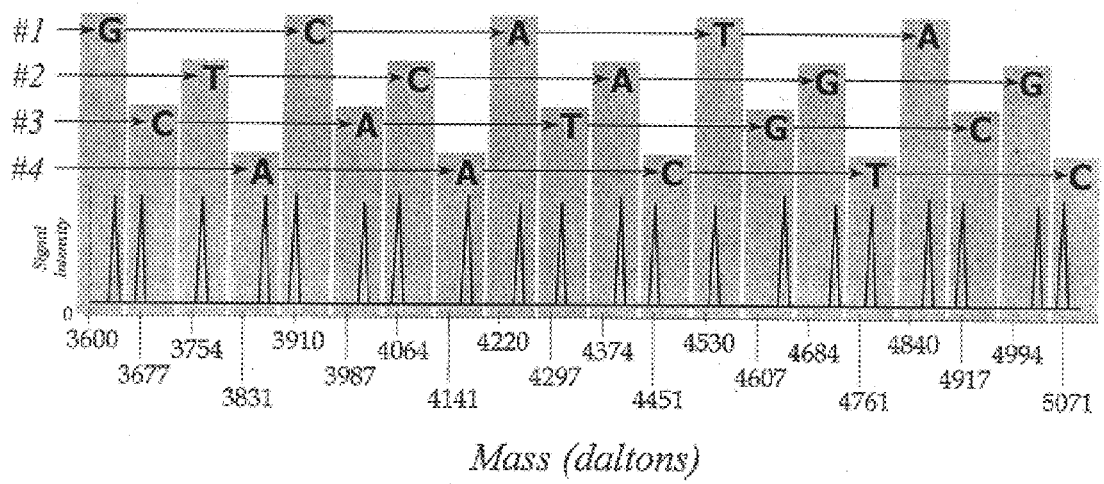
FIG. 3 shows four different sequences resolved in a single spectrum using a set of mass-staggered primers that are separated in mass by integer multiples of 77 daltons (77, 154, and 231 daltons).
Figure 4:
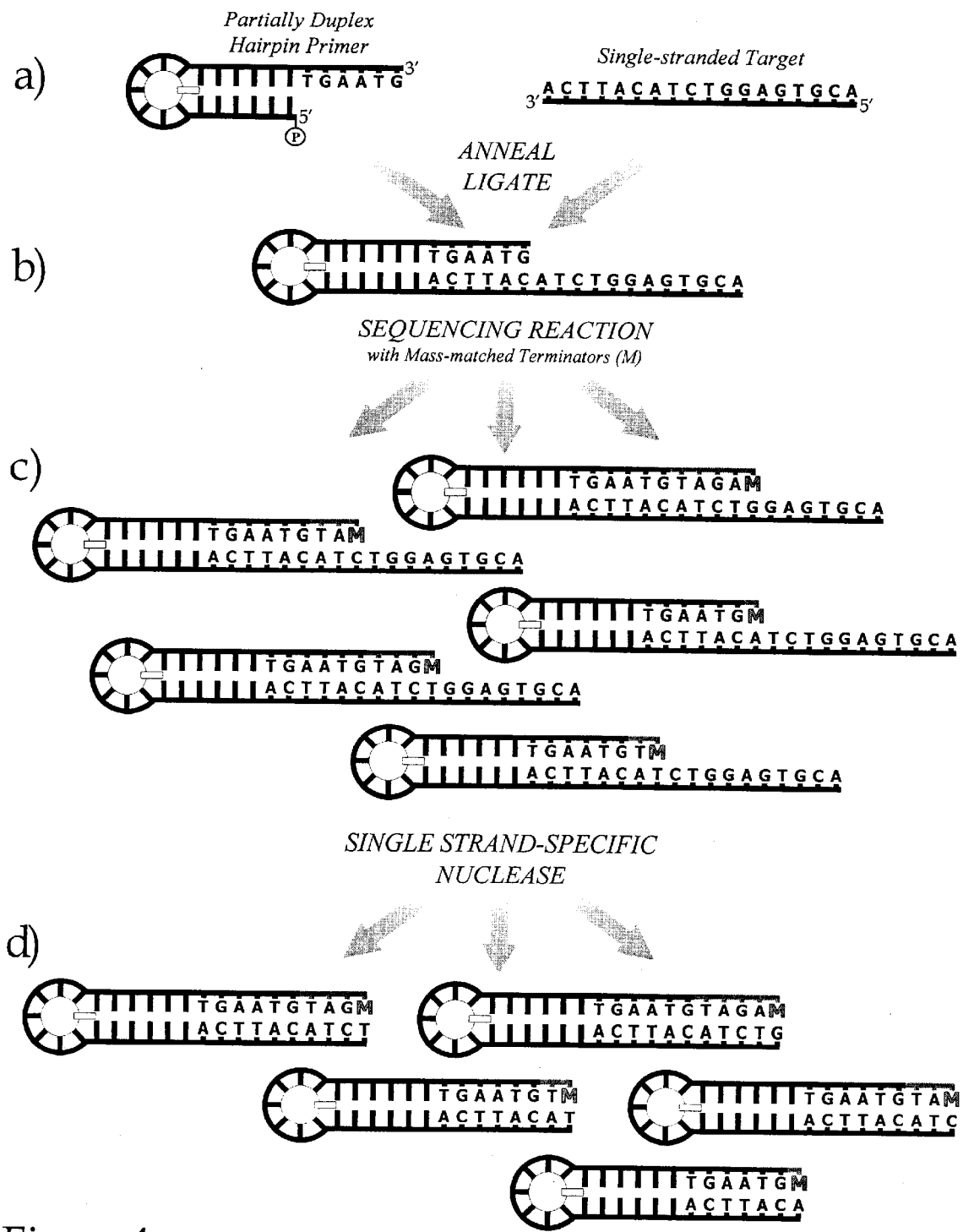
FIG. 4a–d shows the general implementation of a forced mass modulation method using pair-matched nucleotides, for the analysis of sequencing reaction products as double-stranded structures. The steps in the reaction are as follows: a) a partially duplex hairpin primer with a 3' overhang and a 5' phosphate group is annealed and ligated to the single stranded target sequence; b) the resulting partially duplex structure is subjected to a sequencing reaction using the pair-matched nucleotide set described above along with the set of mass-matched terminators (ddM); c) products resulting from sequencing reaction b); and, d) the products c) from the sequencing reaction are exposed to a strict single strand-specific nuclease that results in the production of blunt-ended hairpin structures ready for analysis by mass spectrometry.
Figure 5:
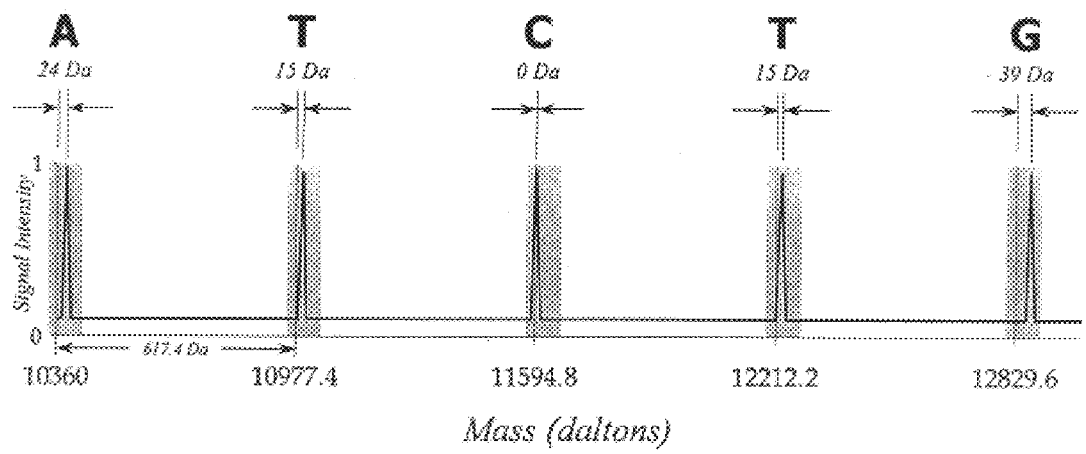
FIG. 5a–b shows the products and molecular masses of the nuclease digestion elucidated in FIG. 4d, along with a simulated mass spectrum.
Figure 6:
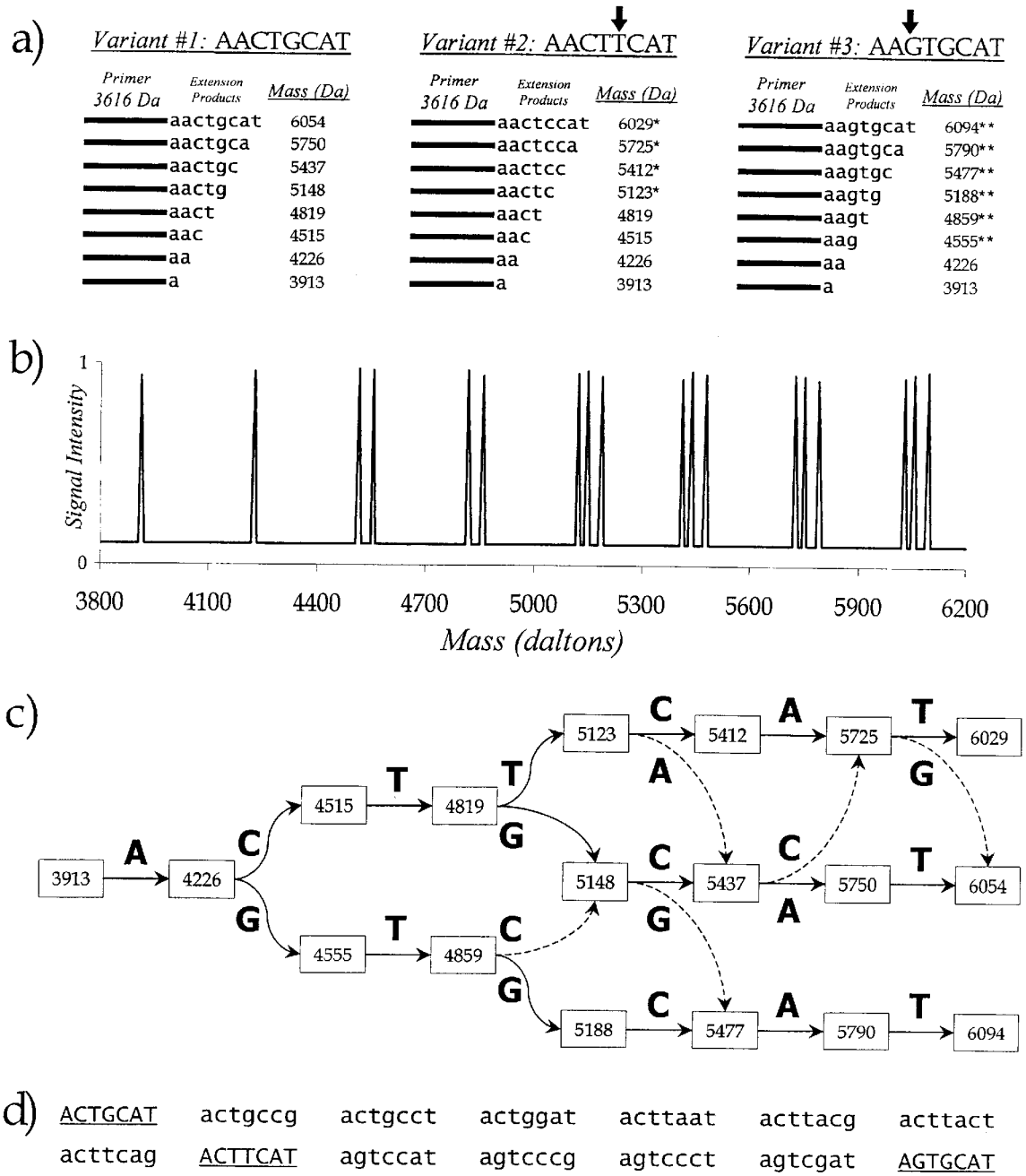
FIG. 6a–d shows three sequence variants (FIG. 6a) that differ from each other only at a single base position sequenced by a conventional Sanger reaction.
Figure 7:
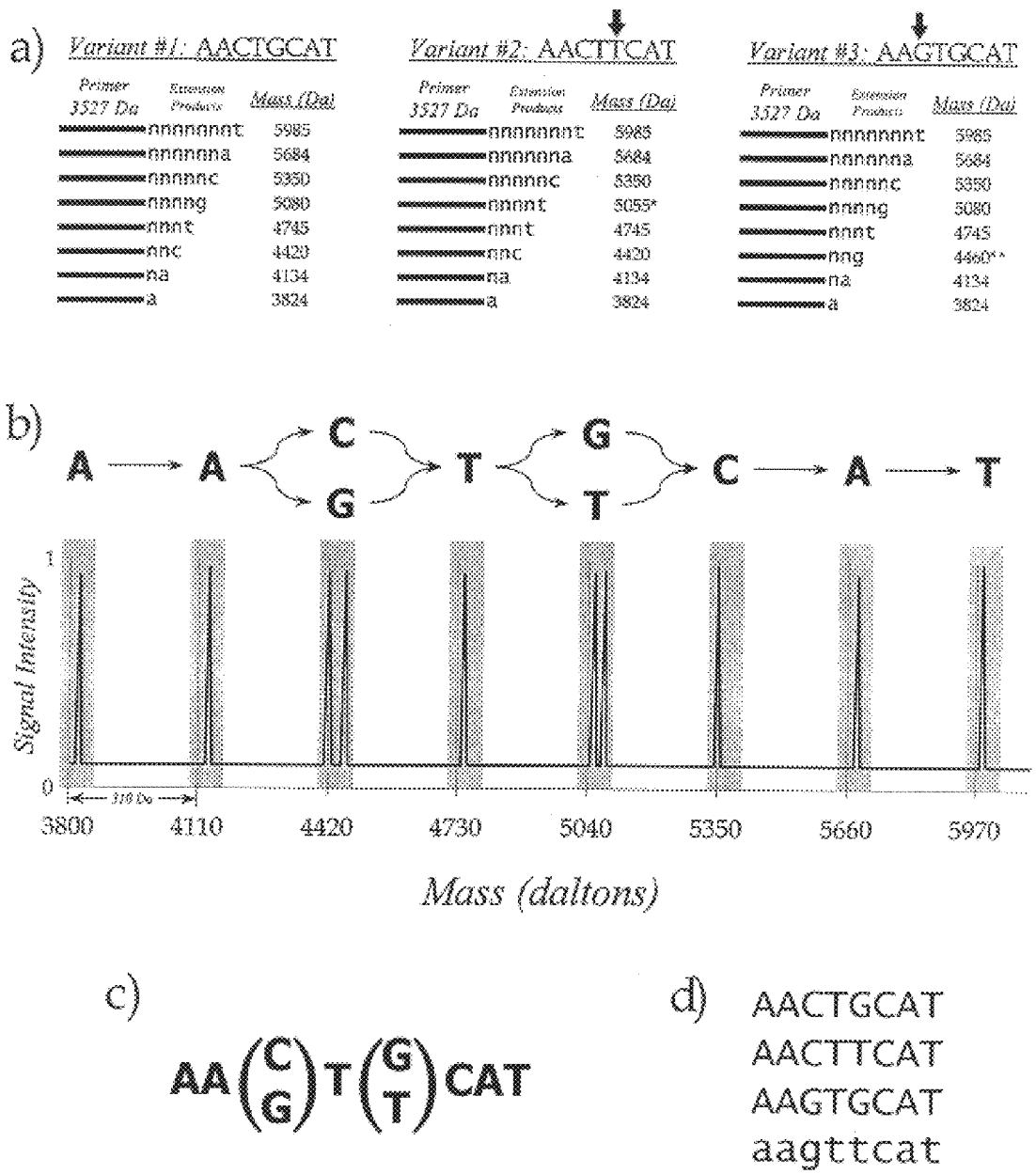
FIG. 7a shows the three related sequence variants from FIG. 6a–d sequenced by Forced Mass Modulation using a single primer and the mass-matched nucleotide set from FIG. 2a–b with the standard dideoxy terminators. The positions of the differing bases are shown by solid arrows. Reaction products are shown along with their respective molecular masses. Reaction products of variant #2 whose masses differ from those of variant #1 are marked with by (*). Reaction products of variant #3 whose masses differ from those of variant #1 are marked by (**).
FIG. 7b is a simulated mass spectrum of all reaction products shown in FIG. 7a along with a sequence graph. The dotted regions represent the only valid mass ranges that can be assumed by the reaction products from FIG. 7a. The base periodicity is 310 daltons.
FIG. 7c is a consensus sequence derived from the data shown in FIG. 7b.
FIG. 7d is an expansion of the consensus sequence shown in FIG. 7c. Spurious reconstructions are shown in lowercase letters, valid ones in uppercase letters. Note that there is only a single spurious reconstruction, as opposed to the eleven errant sequences reconstructed from the Sanger reaction described in FIG. 6a–d.
Figure 2B:
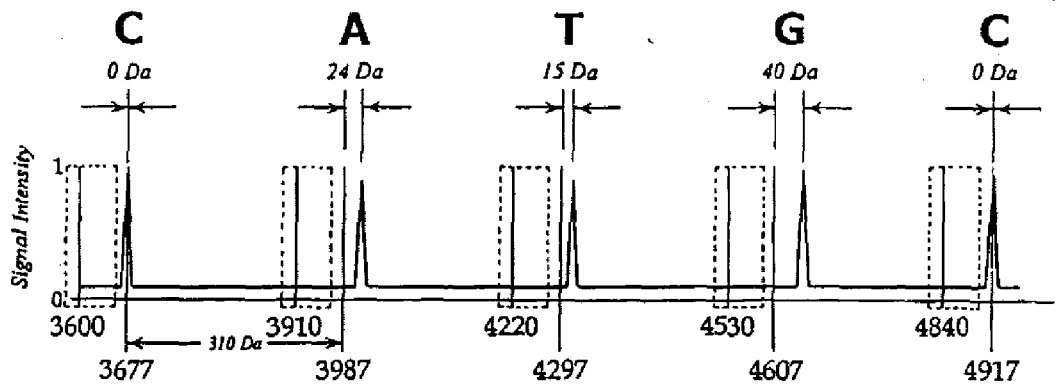
Figure 3:
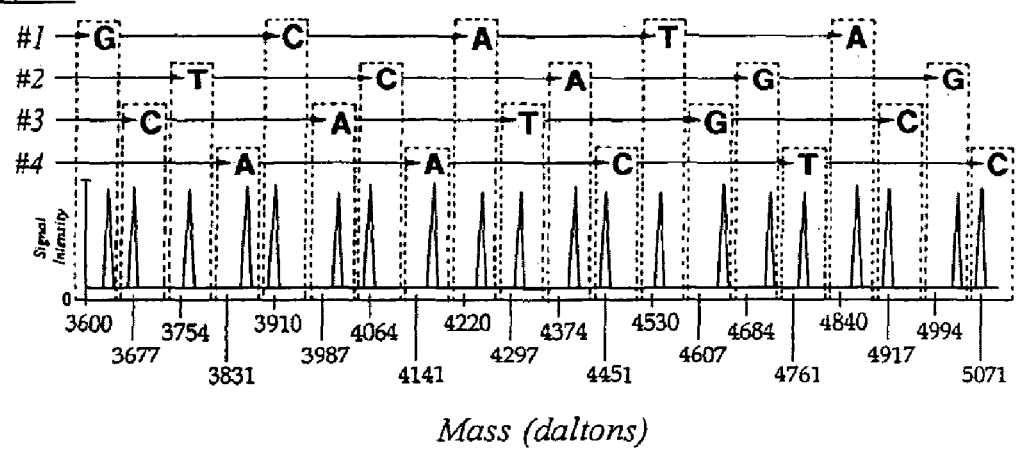
Figure 4A:
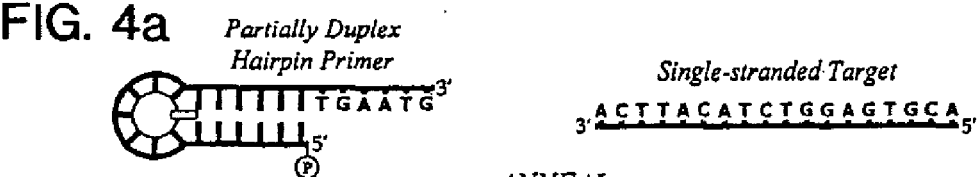
Figure 4B:
Figure 4C:
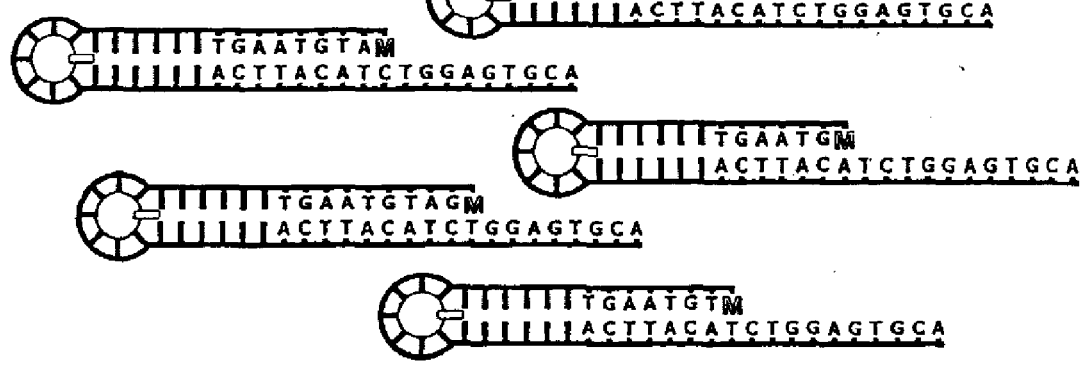
Figure 4D:
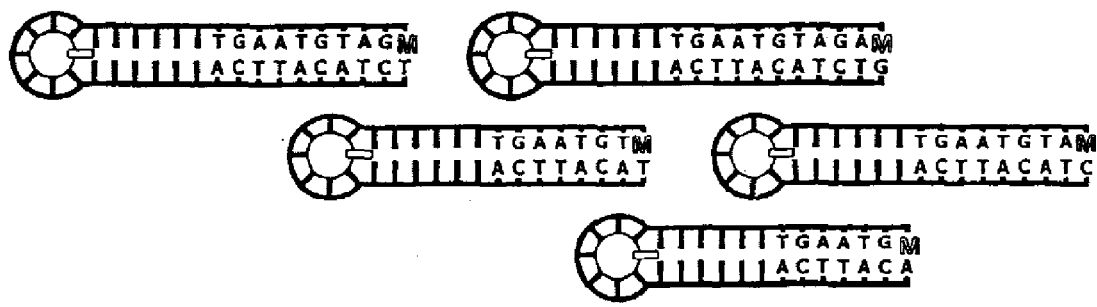

In practice, it is recommended most mass spectrometric formats that the second primer is at least about 60 daltons heavier than the first primer, as each observed peak will have a finite width. FIG. 2b shows a target second sequence resolved on the same mass spectrum shown in FIG. 2a, using a primer heavier by 77 daltons. The peaks corresponding to the reaction products from the first target sequence can fall within the shaded regions of the spectrum in FIG. 2b, which can never intersect peaks from the second target sequence. Unambiguous resolution of both sequences is possible in this arrangement because each peak can be uniquely assigned to a nucleotide, a base position, and a target sequence. This method is designated Mass Spectrum Division Multiplexing herein, and it is implemented using mass-staggered primers. FIG. 3 shows four different sequences resolved in a single spectrum using a set of mass-staggered primers that are separated in mass by integer multiples of 77 daltons (77, 154, and 231 daltons).

The theoretical upper limit on the number of sequences that can be multiplexed in a single mass spectrum is given by the following equation:

$$L' = \frac{P_{base}}{S_{\max}}, \quad (iv)$$

where L' is the upper limit, $P_{base}$ is the base periodicity, and $S_{max}$ is the maximum mass shift in daltons. For the nucleotide set and terminators used in this example, L=(310/40)= 7.75, or approximately seven. Increasing the number of sequences that can be multiplexed in a single spectrum, can be achieved by implementing one or both of an increase in the base periodicity, and a reduction of the maximum mass shift. The base periodicity can be increased by choosing a mass-matched nucleotide set that has a higher molecular weight for dN. It is simpler to lower the maximum mass shift by careful use of the nucleotide terminators and their analogs. For example, if the sequencing reactions were performed using only the terminators ddC, ddT, and ddA, then the maximum mass shift becomes (mass of ddA−mass of ddC)=(297−273)=24 Da. In this case the upper limit on the number of sequences that can be multiplexed is L=(310/ 24)=12.92, or approximately twelve. In situations where complete sequence information is not required, such as diagnostic sequencing, a great reduction in the number of required spectra can be realized by using fewer than four nucleotide terminators. If the sequencing reaction is performed using only a single nucleotide terminator, the maximum mass shift becomes identically zero, and the number of sequences that can be multiplexed in a single spectrum is limited only by the absolute resolution of the mass spectrometer in question. If a given mass spectrometer has an absolute resolution of 12 Da in the mass range of the sequencing reaction products, then the maximum number of sequences that can be multiplexed is given by L=(310/12J= 25.83, or approximately twenty-five.

EXAMPLE 2

Forced Mass Modulation using Pair-Matched Deoxynucleotides

Implementation of Forced Mass Modulation using pair-matched nucleotides is shown in FIG. 4a–d. The basic requirement for this method is that the sequencing reaction products can be analyzed as double-stranded structures.

Figures 5A, 5B:
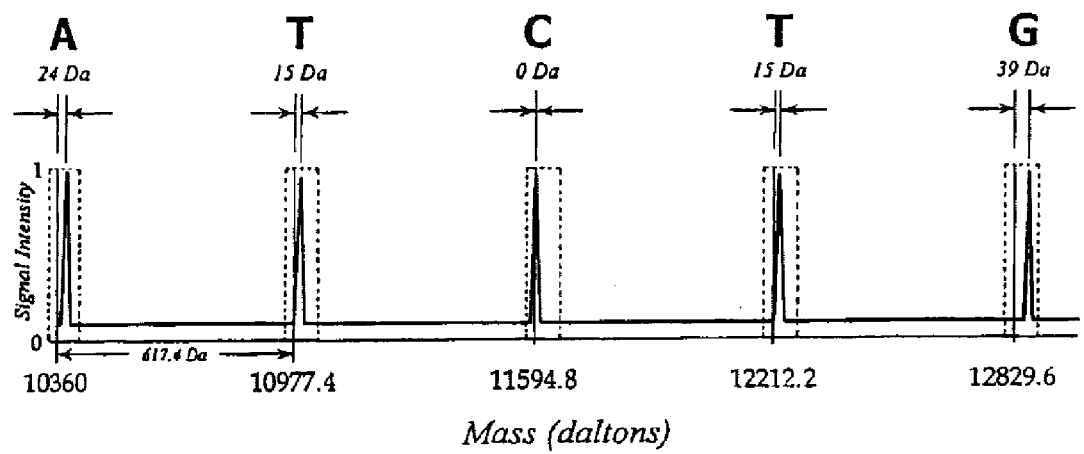
Figures 7A, 7B, 7C, 7D:
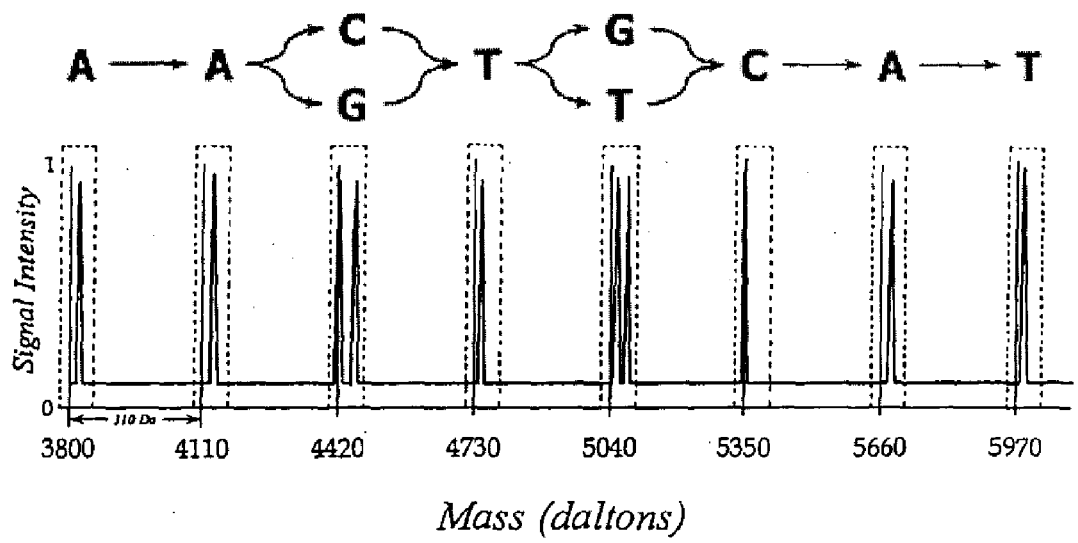

Briefly, the steps in the reaction are as follows: 1) A partially duplex hairpin primer with a 3' overhang and a 5' phosphate group is annealed and ligated to the single stranded target sequence. 2) The resulting partially duplex structure is subjected to a sequencing reaction using the pair-matched nucleotide set described above along with the set of mass-matched terminators (ddM). 3) The products from the sequencing reaction are exposed to a strict single strand-specific nuclease that results in the production of blunt-ended hairpin structures ready for analysis by mass spectrometry. FIG. 5a–b shows the products and molecular masses of the nuclease digestion along with a simulated mass spectrum.

Because the reaction products are double-stranded, they are forced to assume a quasi-periodic distribution with a base periodicity of 617.4 daltons. The dotted regions on the spectrum shown in FIG. 5b indicate the allowed mass ranges that can be occupied by the reaction products. The first periodic reference mass is at 10360 Da, which is the mass of the fully duplex hairpin primer plus a ddM:dG base pair. Expressing the periodic reference masses in terms of the base position n yields:

$$M_{PR}[n]=(M_{duplex}+M_{light}+Mdd_M)+(n-1)\times P_{base} \quad (x)$$

Where $M_{PR}[n]$ is the $n^{th}$ periodic reference mass, $M_{duplex}$ is the mass of the fully duplex primer, $M_{light}$ is the mass of the lightest deoxynucleotide in the target, $P_{base}$ is the base periodicity, and $Mdd_M$ is the mass of ddM in daltons. The observed masses of the sequencing reaction products are given by the following equation:

$$M_{obs}[n]=M_{duplex}+Mdd_M+(n-1)\times P_{base}+M_{targ}[n], \quad (xi)$$

where n is the base position, $M_{obs}[n]$ is the $n^{th}$ observed mass, and $M_{targ}[n]$ is the mass of the $n^{th}$ nucleotide in the target sequence past the priming site in the 3'->5' direction.

In contrast to the mass-matched nucleotide set implementation that provides the sequence complementary to the template strand read in the 5'->3' direction, the pair-matched nucleotide set implementation described herein directly reads the template strand in the 3'->5' direction. The positional mass differences for this implementation are the same as those in Example 1, except that the mass difference corresponding to a termination on dG is 39 as opposed to 40 daltons, because 7-deaza-dG is exactly one dalton lighter than dG. Since double stranded DNA can be analyzed for this method to work, the effective sequence read length is halved, although the number of sequences that can be multiplexed is doubled, due to the increase in the base periodicity.

As a demonstration of Forced Mass Modulation implemented without using mass-matched terminators, the positional mass differences for the above example using the following set of nucleotide terminators is calculated as follows:

The positional mass difference at every base position is given by:

$$M_{diff}[n]=M_{pair}[n]-M_{lightest}, \quad (xii)$$

where $M_{diff}[n]$ is the $n^{th}$ positional mass difference, $M_{pair}[n]$ is the mass of nth terminating base pair, and $M_{lightest}$ is the mass of the lightest terminating base pair in daltons. Substituting in the values from the table above yields:

$M_{diff}[\text{``G''}]=(587.4-587-4)=0$ $M_{diff}[\text{``A''}]=(601.4-587-4)=14$ $M_{diff}[\text{``C''}]=(615.4-587.4)=28$ $M_{diff}[\text{``T''}]=(666.3-587-4)=78.9$ Since each terminating base pair has a unique positional mass difference, the base sequence can be determined unambiguously. The maximum mass shift in this case is 78.9 daltons. When choosing a set of terminating nucleotides it is important to select the set such that the positional mass difference for each base termination is distinct and resolvable by mass.

If modified nucleotide terminators are not used, it is still possible to implement Forced Mass Modulation by carrying out each of the four termination reactions separately using mass-labeled primers rather than modified terminators, combining all reaction products, and then obtaining a mass spectrum. In order to produce the same positional mass differences as shown in Example 1, using a set of pair-matched nucleotides and the standard dideoxy terminators, the following primer mass shifts are required:

| Termination Reaction | Primer Mass |
| --- | --- |
| C | "reference" primer |
| T | reference primer + 15 Da |
| A | reference primer + 24 Da |
| G | reference primer + 39 Da |

This method is essentially equivalent to multiplexing four single-nucleotide sequencing reactions in the same spectrum, except that all the sequencing products originate from the same priming site but terminate on different nucleotides.

EXAMPLE 3

Forced Mass Modulation in the Detection and Scoring of Single Nucleotide Polymorphisms Forced Mass Modulation can be used to simplify the analysis of closely related sequence variants, as is required in the detection and scoring of single nucleotide polymorphisms. FIG. 6a–d shows three sequence variants that differ from each other only at a single base position sequenced by a conventional Sanger reaction. The mass distribution of the reaction products is so complex that it can be uninterpretable, even if the base sequences of the variants are known a priori.

| Terminator | Nucleotide Analog | Mass Base Pairing | Mass of Base Pair |
| --- | --- | --- | --- |
| T | 5-Bromo-dideoxyuridine | 353.1 5-Br-ddU:dA | 666.3 |
| C | 5-Methyl-dideoxycytidine | 287.2 5-Me-ddC:7-deaza-dG | 615.4 |
| A | Dideoxyadenosine | 297.2 ddA:dT | 601.4 |
| G | Dideoxyinosine | 298.2 ddI:dC | 587.4 |

FIG. 7a–d shows the same three variants sequenced by Forced Mass Modulation using mass-matched deoxynucleotides (dN=310 Da) and the standard dideoxy terminators. The positions and identities of the single-nucleotide changes are immediately apparent from the mass spectrum. Since the masses of the sequencing reaction products are constrained to fall within the shaded regions of the spectrum in FIG. 7b, it is possible to multiplex other sequences on the same spectrum.

EXAMPLE 4

Figure 8:
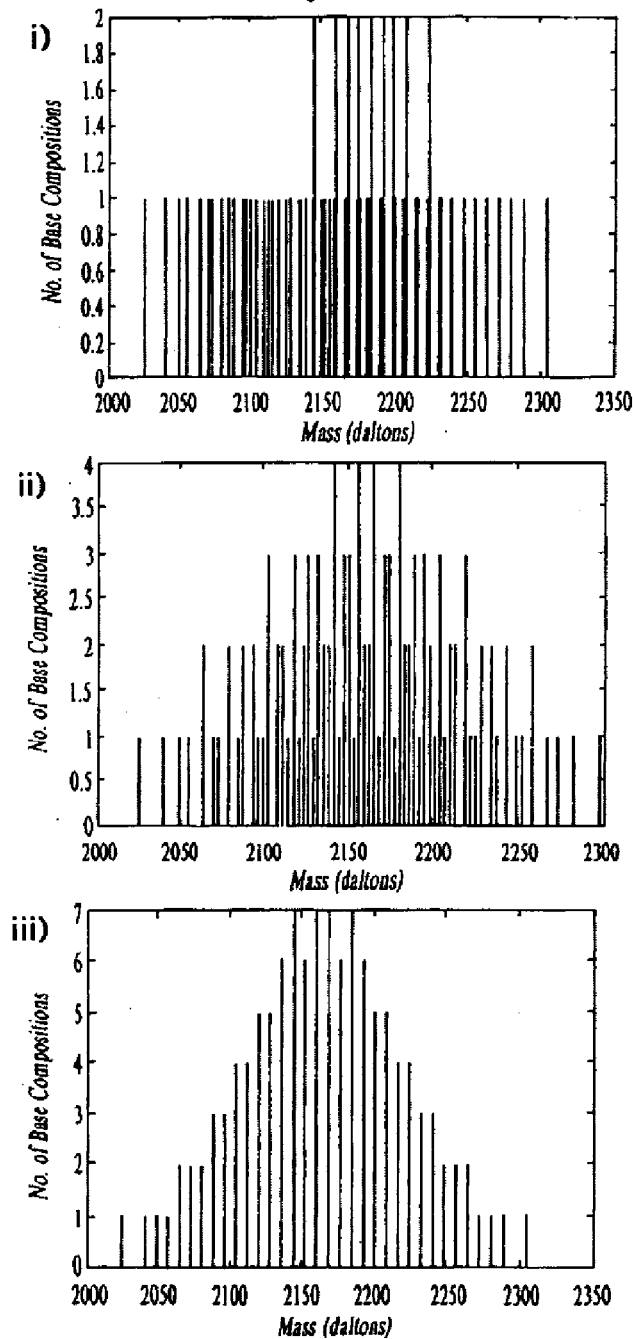
FIG. 8i–iii shows the base composition density distributions for the total set of possible 7-base oligonucleotides using three different nucleotide sets. Note that for the set of naturally occurring bases, nearly every base composition has its own distinct mass value, but most of these mass values are spaced only one dalton from each other. Increasing the peak separation also markedly increases the average number of base compositions per observed mass, particularly for those masses in the center of the range.

Base Composition Density Distributions for the Total Set of Possible 7-Base Oligonucleotides For this implementation, three sets of 7-base oligonucleotides comprising all possible base compositions for a 7-base oligonucleotide can be obtained; the first set comprising the four natural bases (dA, dG, dO and dT), the second set comprising three of the natural bases (dA, dC and dT) and the nucleotide analog 7-deaza-deoxyguanosine (7-deaza-dG) substituted for dG, and the third set comprising three of the natural bases (dA, dG and dC) and the nucleotide analog deutero-deoxythymine (deutero-dT) substituted for dT. FIG. 8*i–iii* shows the actual base composition density distributions for the total set of possible 7-base oligonucleotides using the three different nucleotide sets. Note that for the set of naturally occurring bases (FIG. 8*i*), nearly every base composition has its own distinct mass value, but most of these mass values are spaced only one dalton from each other. Increasing the peak separation to three daltons by substitution of dG with 7-deaza-dG (FIG. 8*ii*) markedly increases the average number of base compositions per observed mass, particularly for those masses in the center of the range, but any two oligonucleotides of the same length with different molecular weights will have to be separated by at least three daltons. Similarly, substitution of dT with deutero-dT (FIG. 8*iii*) gives a minimum peak separation between oligonucleotides having the same length but different molecular weights of eight daltons. The trade-off for a greater peak separation is a greater number of oligonucleotides that have exactly the same mass for a given oligonucleotide length.

Since modifications will be apparent to those of skill in this art, it is intended that this invention be limited only by the scope of the appended claims.

determining the mass of each extension product; and calculating a mass shift from a period for the mass of each extension product, whereby nucleotide(s) at one or more base positions is determined by identifying the nucleotide that corresponds to each mass shift.

2. The method of claim 1 that is a method for determining a nucleotide sequence of a target nucleic acid, comprising:

synthesizing extension products of the target nucleic acid in the presence of chain terminating nucleotides and mass-matched nucleotides;

determining the mass of each extension product; and calculating a mass shift from a period for the mass of each extension product, whereby the nucleotide sequence of the target nucleic acid is determined by assigning a nucleotide corresponding to each mass shift.

3. The method of claim 1, wherein the mass-matched deoxynucleotides are identical.

4. The method of claim 1, wherein a mass-matched deoxynucleotide is deoxyinosine, 5-nitroindole, 3-nitropyrrole, 3-methyl 7-propynyl isocarbostyril, 5-methyl isocarbostyril or 3-methyl isocarbostyril.

5. A method for identifying nucleotides at one or more base positions in a plurality of target nucleic acid molecules, comprising:

synthesizing extension products of the target nucleic acid in the presence of chain terminating nucleotides and mass-matched nucleotides;

determining the mass of each extension product; and calculating a mass shift from a period for the mass of each extension product, whereby the nucleotides in the target nucleic acid molecules are identified by determining the nucleotide that corresponds to each mass shift.

6. The method of claim 5 that is a method for determining nucleotide sequences of a plurality of target nucleic acid molecules, comprising:

synthesizing extension products of the target nucleic acid in the presence of chain terminating nucleotides and mass-matched nucleotides;

determining the mass of each extension product; and

What is claimed is:

1. A method for identifying the nucleotide at one or more base positions in a target nucleic acid molecule, comprising:

synthesizing extension products of the target nucleic acid in the presence of chain terminating nucleotides and mass-matched nucleotides;

calculating a mass shift from a period for the mass of each extension product, whereby the nucleotide sequences of the target nucleic acids are determined by determining the nucleotide that corresponds to each mass shift.

7. The method of claim 5, wherein the mass-matched deoxynucleotides are identical to one another.

8. The method of claim 5, wherein a mass-matched deoxynucleotide is deoxyinosine, 5-nitroindole, 3-nitropyrrole, 3-methyl 7-propynyl isocarbostyril, 5-methyl isocarbostyril or 3-methyl isocarbostyril.

9. A method for determining a nucleotide sequence of a target nucleic acid molecule, comprising:
   incorporating pair-matched nucleotides into the target nucleic acid;
   synthesizing extension products of the target nucleic acid in the presence of a partially duplex hairpin primer, chain terminating nucleotides and pair-matched nucleotides;
   determining the mass of each extension product; and
   calculating a mass shift from a period for the mass of each extension product;
   whereby the nucleotide sequence of the target nucleic acid is determined by assigning a nucleotide corresponding to each mass shift.

10. The method of claim 9, wherein the chain terminating nucleotides are mass-matched.

11. The method of claim 9, wherein the chain terminating nucleotide base pairs have distinct molecular weights.

12. A method for determining nucleotide sequences of a plurality of target nucleic acids, comprising:
   incorporating pair-matched nucleotides into the target nucleic acids;
   synthesizing extension products of the target nucleic acids in the presence of a partially duplex hairpin primer, chain terminating nucleotides and pair-matched nucleotides;
   amplifying the target nucleic acid sequences in the presence of pair-matched nucleotides;
   determining the mass of each extension product; and
   calculating a mass shift from a period for the mass of each extension product;
   whereby the nucleotide sequences of the target nucleic acids are determined by assigning a nucleotide corresponding to each mass shift.

13. The method of claim 12, wherein the chain terminating nucleotides are mass-matched.

14. The method of claim 12, wherein the chain terminating nucleotide base pairs have distinct molecular weights.

15. The method of claim 12, wherein the primers are mass-labeled.

16. A method for detecting one or a plurality of target nucleic acid(s) molecules or one or a plurality of nucleotides therein, comprising:
   (a) copying the target nucleic acid molecule(s) in the presence of a pair-matched set of nucleotides;
   (b) denaturing the resulting copies of the target(s) to produce single-stranded templates;
   (c) annealing and ligating one or a plurality of partially duplex hairpin primers to the single-stranded template(s);
   (d) extending the primer(s) in the presence of chain terminating nucleotides and pair-matched nucleotides to produce extension products, wherein the extension products follow a periodic mass distribution that is determined by the mass of the pair-matched nucleotide set; and
   (e) detecting each of the targets or nucleotides therein by virtue of the mass shift of each extension product from its corresponding periodic reference mass.

17. The method of claim 16, wherein the chain terminating nucleotides are mass-matched.

18. The method of claim 16, wherein the chain terminating nucleotide base pairs have distinct molecular weights.

19. The method of claim 16, wherein the primers are mass-labeled.

20. A method for detecting different nucleotide base compositions in a population of nucleic acids having identical length, comprising:
   synthesizing the nucleic acids in the presence of one or more nucleotide analogs to produce synthesized nucleic acids; and
   determining a mass of each synthesized nucleic acid;
   whereby different nucleotide base compositions are detected by determining the mass of each synthesized nucleic acid,
   wherein the nucleotide analog separates the masses of nucleic acids having different base compositions in a predetermined interval.

21. The method of claim 20, wherein the population of nucleic acids having identical length and different base compositions differ in base composition by a single base.

22. A method for detecting a plurality of target nucleic acid molecules in a sample containing nucleic acid molecules, comprising:
   preparing a composition containing a plurality of pair-matched nucleic acid molecules or mass-matched nucleic acid molecules from a sample comprising the target nucleic acid molecules;
   analyzing the resulting composition by mass spectrometry; and
   detecting target nucleic acid molecules.

23. A process for detecting a mutation in a target nucleic acid sequence in a target nucleic acid molecule, in a sample, comprising:
   a) hybridizing a primer to nucleic acid molecules in the sample, thereby producing a hybridized primer and a molecule from the sample, wherein:
      the nucleic molecules from the sample are optionally immobilized and
      the primer is complementary to a sequence in the target nucleic acid sequence that is adjacent to the region suspected of containing a mutation sequence;
   b) contacting the hybridized primer with a composition comprising mass-matched deoxyriboflucleoside triphosphates and a chain terminating nucleotide selected from a dideoxyribonucleoside triphosphate or a 3'-deoxynucleoside triphosphate and optionally one or more deoxyribonucleoside triphosphates, such that the hybridized primer is extended until a chain terminating nucleotide is incorporated, thereby producing an extended primer; and
   c) determining the mass of the extended primer, thereby determining whether a mutation is present in the target nucleic acid sequence.

24. The process of claim 23, wherein the chain terminating nucleotides are mass-matched.

25. The method of claim 23, wherein the mass of the extended primer is determined by mass spectrometry.

26. A process for detecting mutations in a plurality of target nucleic acid sequences in a sample, comprising:
   a) hybridizing a plurality of primers to nucleic acid molecules in the sample, thereby producing hybridized primers, wherein:
      the nucleic acid molecules from the sample are optionally immobilized and each primer is complementary to a sequence of a target nucleic acid sequence that is adjacent to a region suspected of containing a mutation sequence;

b) contacting the hybridized primers with a composition comprising a chain terminating nucleotide selected from a mass-matched dideoxyribonucleoside triphosphate or a 3'-deoxynucleoside triphosphate and one or more deoxyribonucleoside triphosphates, such that the hybridized primers are extended until a chain terminating nucleotide is incorporated, thereby producing an extended primer; and c) determining the mass of the extended primers, thereby determining whether mutations are present in the target nucleic acid sequences.

27. The process of claim 26, wherein the chain terminating nucleotides are mass-matched.

28. The method of claim 26, wherein the masses of the extended primers are determined by mass spectrometry.

29. A method for detecting a target nucleic acid sequence, comprising the steps of:

a) hybridizing a primer to a nucleic acid molecule comprising a target nucleic acid sequence, wherein the primer can be extended in a 3' direction towards the target nucleic acid sequence, and wherein the 5' end of the primer can be selectively cleaved from the extension product;

b) extending the primer in the presence of mass matched deoxyribonucleotides and a polymerase to produce an extension product;

c) selectively cleaving the 5' end of the primer from the extension product to produce a portion of the primer and a cleaved extension product; and d) detecting the cleaved extension product.

30. The method of claim 29, wherein the cleaved extension product is detected by mass spectrometry.

31. A method for detecting a plurality of target nucleic acid sequences, comprising the steps of:

a) hybridizing a primer or plurality thereof to nucleic acid molecules comprising target nucleic acid sequences, wherein the primers can be extended in a 3' direction towards the target nucleic acid sequence, and wherein the 5' end of the hybridized mass-matched nucleic acid molecules can be selectively cleaved from the extension product;

b) extending the primers in the presence of mass matched deoxyribonucleotides and a polymerase to produce extension products;

c) selectively cleaving the 5' end of the primers from the extension products to produce portions of the primers and cleaved extension products; and d) detecting the cleaved extension products.

32. The method of claim 31, wherein the cleaved extension product is detected by mass spectrometry.

33. A method for detecting a target nucleic acid sequence, comprising the steps of:

a) hybridizing to a nucleic acid molecule comprising the target nucleic acid sequence
a first primer, which can be extended in a 3' direction towards the target nucleic acid sequence, and wherein the 5' end of the primer can bee selectively cleaved from the extension product, and
a second primer, which can be extended in a 3' direction towards the first primer;

b) extending the primers in the presence of mass-matched nucleotides to produce a double stranded amplification product;

c) selectively cleaving the 5' end of the first primer in the amplification product, to product a double stranded amplification product comprising a cleaved primer extension product comprising a 5' portion and a 3' portion;

d) denaturing the product of step c); and e) detecting the 3' portion of the cleaved primer extension product.

34. The method of claim 33, wherein the cleaved extension product is detected by mass spectrometry.

35. A method for detecting a plurality of target nucleic acid sequences, comprising:

a) hybridizing to each of a plurality of nucleic acid molecules comprising the target nucleic acid sequence
a first primer, which can be extended in a 3' direction towards the target nucleic acid sequence, and wherein the 5' end of the primer can be selectively cleaved from the extension product, and
a second primer, which can be extended in a 3' direction towards the first primer;

b) extending the primers in the presence of mass-matched nucleotides or pair-matched nucleotides to produce double stranded amplification products;

c) selectively cleaving the 5' end of each of the first primers in the amplification product, to produce double stranded amplification products comprising cleaved primer extension products comprising a 5' portion and a 3' portion;

d) denaturing the products of step c); and e) detecting the 3' portions of the cleaved primer extension products by virtue of the masses.

36. The method of claim 35, wherein detection is effected by mass spectrometry.

37. A method for detecting a target nucleic acid sequence, comprising:

a) hybridizing first and second primers to a nucleic acid molecule containing the target nucleic acid sequence, wherein a primer contains a selectively cleavable site at its 3' end;

b) extending the primers in the presence of mass-matched nucleotides;

c) cleaving the resulting product at the selectively cleavable sites; and d) analyzing the masses of the cleavage products, whereby the target sequence is detected.

38. The method of claim 37, wherein the cleaved extension product is detected by mass spectrometry.

39. The process of claim 38, wherein a plurality of primers are hybridized and a plurality of target sequences are identified in a single reaction.

40. The method of claim 39, wherein the cleaved extension products are detected by mass spectrometry.

* * * * *

UNITED STATES PATENT AND TRADEMARK OFFICE
CERTIFICATE OF CORRECTION

PATENT NO.    : 6,660,229 B2
DATED         : December 9, 2003
INVENTOR(S)   : Cantor et al.

It is certified that error appears in the above-identified patent and that said Letters Patent is hereby corrected as shown below:

Drawings,
Please replace Figures 1a-8 with the Formal Figures 1a-8.

Signed and Sealed this

Twelfth Day of October, 2004

JON W. DUDAS
*Director of the United States Patent and Trademark Office*

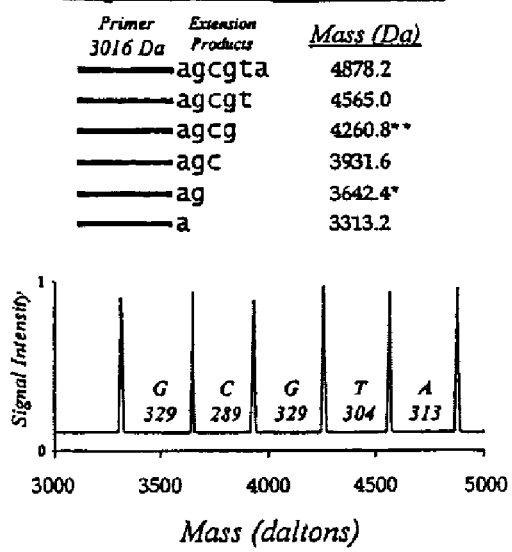
FIG. 1a
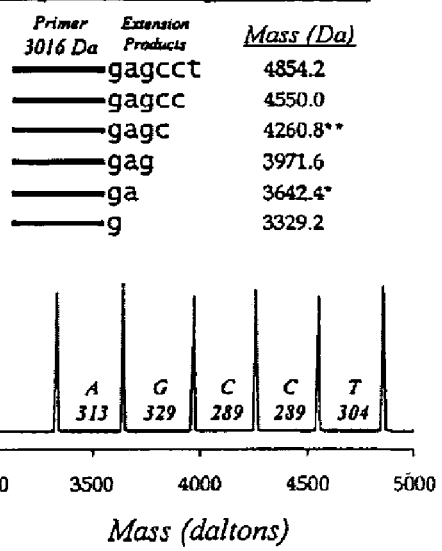
FIG. 1b
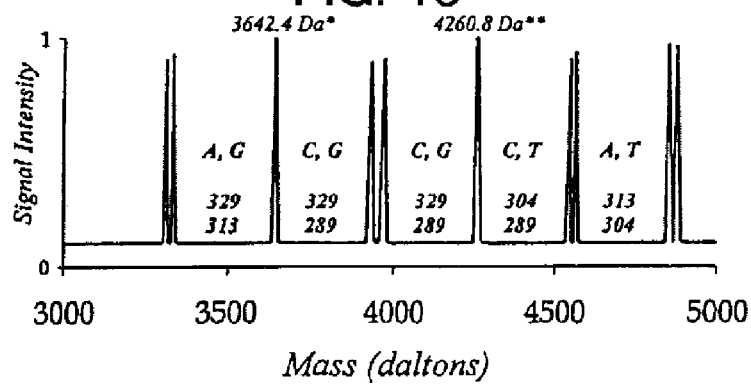
FIG. 1c
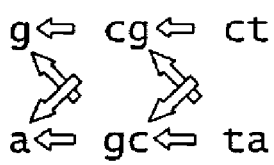
FIG. 1d
```
gcgct
GCGTA
ggcct
ggcta
acgct
acgta
AGCCT
agcta
```
FIG. 1e

*Partially Duplex Hairpin Primer*

*Single-stranded Target*

ANNEAL LIGATE

SEQUENCING REACTION
with Mass-matched Terminators (M)

SINGLE STRAND-SPECIFIC NUCLEASE

| Variant #1: AACTGCAT | Variant #2: AACTTCAT ↓ | Variant #3: AAGTGCAT ↓ |
|---|---|---|
| Primer 3616 Da / Extension Products / Mass (Da) | Primer 3616 Da / Extension Products / Mass (Da) | Primer 3616 Da / Extension Products / Mass (Da) |
| aactgcat 6054 | aactccat 6029* | aagtgcat 6094** |
| aactgca 5750 | aactcca 5725* | aagtgca 5790** |
| aactgc 5437 | aactcc 5412* | aagtgc 5477** |
| aactg 5148 | aactc 5123* | aagtg 5188** |
| aact 4819 | aact 4819 | aagt 4859** |
| aac 4515 | aac 4515 | aag 4555** |
| aa 4226 | aa 4226 | aa 4226 |
| a 3913 | a 3913 | a 3913 |

FIG. 6a

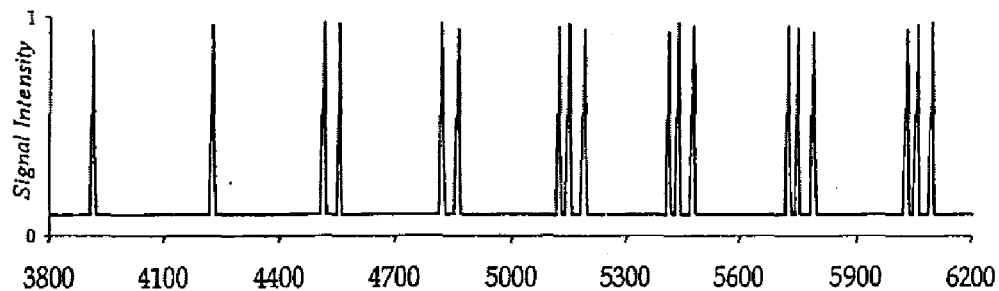

FIG. 6b   *Mass (daltons)*

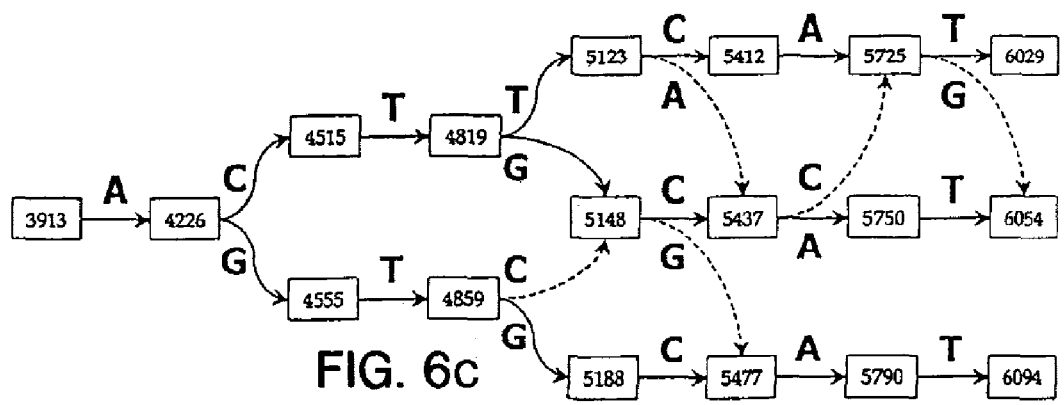

FIG. 6c

| <u>ACTGCAT</u> | actgccg | actgcct | actggat | acttaat | acttacg | acttact |
| acttcag | <u>ACTTCAT</u> | agtccat | agtcccg | agtccct | agtcgat | <u>AGTGCAT</u> |

FIG. 6d

AACTGCAT
AACTTCAT
AAGTGCAT
aagttcat